(12) United States Patent
Kriesel et al.

(10) Patent No.: US 7,837,653 B2
(45) Date of Patent: Nov. 23, 2010

(54) FLUID DELIVERY APPARATUS WITH VIAL FILL

(75) Inventors: Marshall S. Kriesel, Saint Paul, MN (US); Joshua W. Kriesel, San Francisco, CA (US); Alan D. Langerud, Saint Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 34 days.

(21) Appl. No.: 11/353,761

(22) Filed: Feb. 13, 2006

(65) Prior Publication Data

US 2006/0195057 A1    Aug. 31, 2006

Related U.S. Application Data

(60) Provisional application No. 60/654,671, filed on Feb. 18, 2005.

(51) Int. Cl.
*A61M 5/20* (2006.01)
(52) U.S. Cl. .................. 604/134; 604/131; 604/135; 604/151; 604/207; 604/211; 604/216
(58) Field of Classification Search ............ 604/131, 604/132, 151–153, 890.1, 246–248, 133–135, 604/207, 211, 212, 214, 216, 218; 128/DIG. 12
See application file for complete search history.

(56) References Cited

U.S. PATENT DOCUMENTS

| | | | |
|---|---|---|---|
| 3,731,681 A | 5/1973 | Blackshear et al. |
| 4,381,006 A | 4/1983 | Genese |
| 4,525,165 A | 6/1985 | Fischell |
| 4,557,728 A | 12/1985 | Sealfon et al. |
| 4,608,042 A | 8/1986 | Vanderveen et al. |
| 4,681,566 A | 7/1987 | Fenton, Jr. et al. |
| 4,755,172 A | 7/1988 | Baldwin |
| 4,772,263 A | 9/1988 | Dorman et al. |
| 4,850,807 A | 7/1989 | Frantz |
| 4,863,429 A | 9/1989 | Baldwin |
| 5,014,750 A | 5/1991 | Winchell et al. |
| 5,098,377 A | 3/1992 | Borsanyi et al. |
| 5,100,389 A | 3/1992 | Vaillancourt |

(Continued)

*Primary Examiner*—Kevin C Sirmons
*Assistant Examiner*—Laura C Schell

(57) ABSTRACT

A compact fluid dispenser for use in controllably dispensing fluid medicaments, such as antibiotics, analgesics, and the like medicinal agents from the reservoir of the device. Uniquely, the dispenser includes a novel bellows-type reservoir and vial fill means for filling the bellows-type reservoir with the medicament to be dispensed. The dispenser also includes a novel stored energy source in the form of a constant force spring which controllably urges the medicinal fluid from the device reservoir. Additionally, the apparatus of the invention includes a novel adjustable flow rate control assembly that is disposed intermediate the fluid reservoir outlet and the outlet port of the device for precisely controlling the rate of fluid flow from the outlet port toward the patient. The rate control assembly includes a rate selector member for selecting the desired rate of fluid flow toward the patient and a cooperatively associated flow control plate having a plurality of fluidic micro-channels which controls the rate of fluid flow toward the selector member. The rate control plate uniquely includes a priming feature for priming the various fluid passageways of the device and purging the fluid passageways of gases that may be contained therein prior to the delivery of the medicinal fluids to the administration line of the device.

23 Claims, 15 Drawing Sheets

U.S. PATENT DOCUMENTS

| | | | |
|---|---|---|---|
| 5,176,641 A | 1/1993 | Idriss | |
| 5,205,820 A | 4/1993 | Kriesel | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,336,188 A | 8/1994 | Kriesel | |
| 5,346,476 A | 9/1994 | Elson | |
| 5,380,287 A * | 1/1995 | Kikuchi et al. | 604/135 |
| 5,411,480 A | 5/1995 | Kriesel | |
| 5,419,771 A | 5/1995 | Kriesel | |
| 5,484,410 A | 1/1996 | Kriesel et al. | |
| 5,499,968 A | 3/1996 | Milijasevic et al. | |
| 5,514,090 A | 5/1996 | Kriesel et al. | |
| 5,545,139 A | 8/1996 | Kriesel | |
| 5,620,420 A | 4/1997 | Kriesel | |
| 5,693,018 A | 12/1997 | Kriesel et al. | |
| 5,693,019 A | 12/1997 | Kriesel | |
| 5,720,729 A | 2/1998 | Kriesel | |
| 5,721,382 A | 2/1998 | Kriesel et al. | |
| 5,735,818 A | 4/1998 | Kriesel et al. | |
| 5,741,242 A | 4/1998 | Kriesel | |
| 5,743,879 A | 4/1998 | Kriesel | |
| 5,766,149 A | 6/1998 | Kriesel et al. | |
| 5,779,676 A | 7/1998 | Kriesel et al. | |
| 5,807,323 A | 9/1998 | Kriesel et al. | |
| 5,836,484 A | 11/1998 | Gerber | |
| 5,858,005 A | 1/1999 | Kriesel | |
| 5,885,250 A | 3/1999 | Kriesel et al. | |
| 5,897,530 A | 4/1999 | Jackson | |
| 5,921,962 A | 7/1999 | Kriesel et al. | |
| 5,925,017 A | 7/1999 | Kriesel et al. | |
| 5,957,891 A | 9/1999 | Kriesel et al. | |
| 5,993,425 A | 11/1999 | Kriesel | |
| 6,010,482 A | 1/2000 | Kriesel et al. | |
| 6,027,472 A | 2/2000 | Kriesel et al. | |
| 6,030,363 A | 2/2000 | Kriesel | |
| 6,045,533 A | 4/2000 | Kriesel et al. | |
| 6,063,059 A | 5/2000 | Kriesel | |
| 6,068,613 A | 5/2000 | Kriesel et al. | |
| 6,068,614 A | 5/2000 | Kimber et al. | |
| 6,086,561 A | 7/2000 | Kriesel et al. | |
| 6,090,071 A | 7/2000 | Kriesel | |
| 6,095,491 A | 8/2000 | Kriesel | |
| 6,126,637 A | 10/2000 | Kriesel et al. | |
| 6,126,642 A * | 10/2000 | Kriesel et al. | 604/207 |
| 6,152,898 A | 11/2000 | Olsen | |
| 6,159,180 A | 12/2000 | Kriesel et al. | |
| 6,176,845 B1 | 1/2001 | Kriesel et al. | |
| 6,183,441 B1 * | 2/2001 | Kriesel et al. | 604/132 |
| 6,190,359 B1 | 2/2001 | Heruth | |
| 6,210,368 B1 | 4/2001 | Rogers | |
| 6,236,624 B1 | 5/2001 | Kriesel et al. | |
| 6,245,041 B1 | 6/2001 | Kriesel | |
| 6,258,062 B1 | 7/2001 | Thielen et al. | |
| 6,270,481 B1 | 8/2001 | Mason et al. | |
| 6,273,133 B1 | 8/2001 | Williamson et al. | |
| 6,277,095 B1 | 8/2001 | Kriesel et al. | |
| 6,293,159 B1 | 9/2001 | Kriesel et al. | |
| 6,319,235 B1 | 11/2001 | Yoshino | |
| 6,355,019 B1 | 3/2002 | Kriesel et al. | |
| 6,391,006 B1 | 5/2002 | Kriesel et al. | |
| 6,394,980 B2 | 5/2002 | Kriesel et al. | |
| 6,398,760 B1 | 6/2002 | Danby | |
| 6,416,495 B1 * | 7/2002 | Kriesel et al. | 604/132 |
| 6,485,461 B1 | 11/2002 | Mason et al. | |
| 6,537,249 B2 | 3/2003 | Kriesel et al. | |
| 6,542,350 B1 | 4/2003 | Rogers | |
| 6,569,125 B2 | 5/2003 | Jepson et al. | |
| 6,645,175 B2 | 11/2003 | Kriesel et al. | |
| 6,669,668 B1 | 12/2003 | Kleeman et al. | |
| 7,029,455 B2 | 4/2006 | Flaherty | |

* cited by examiner

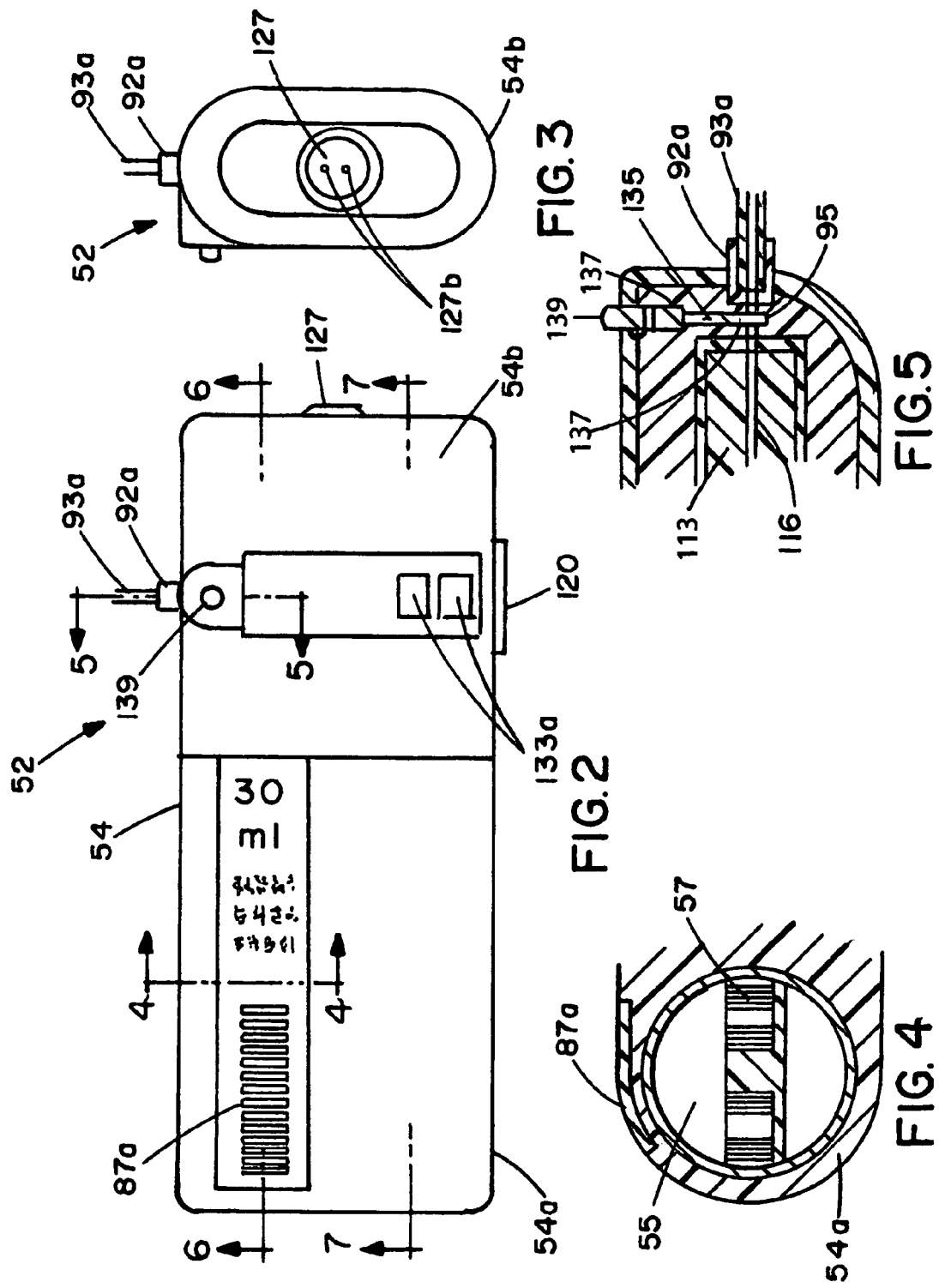

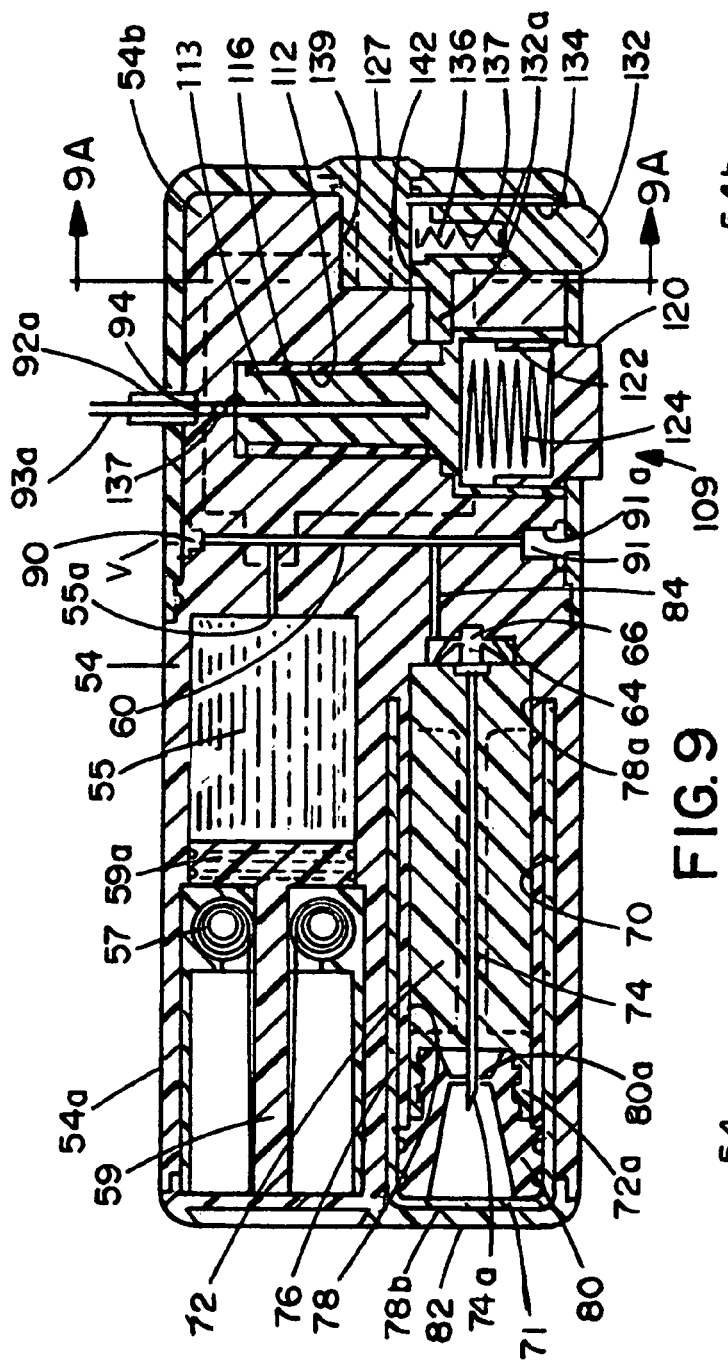
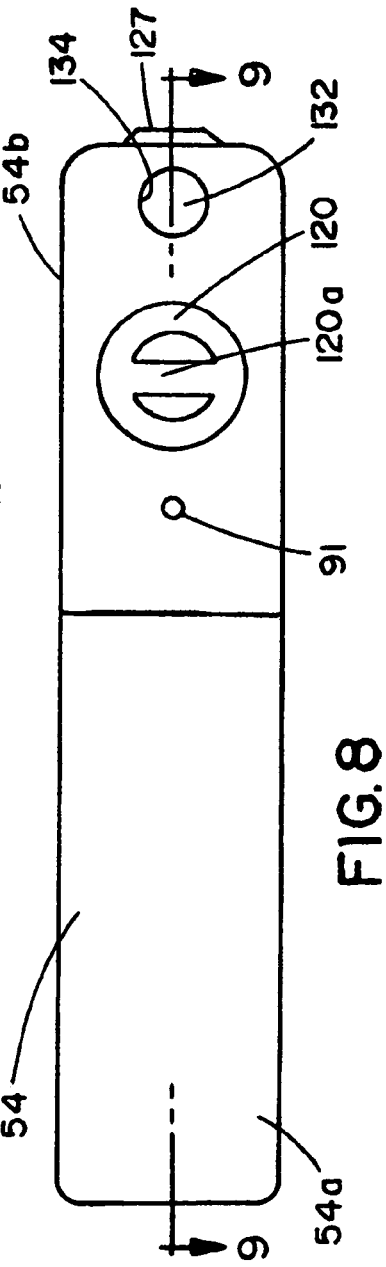
FIG.9
FIG.8

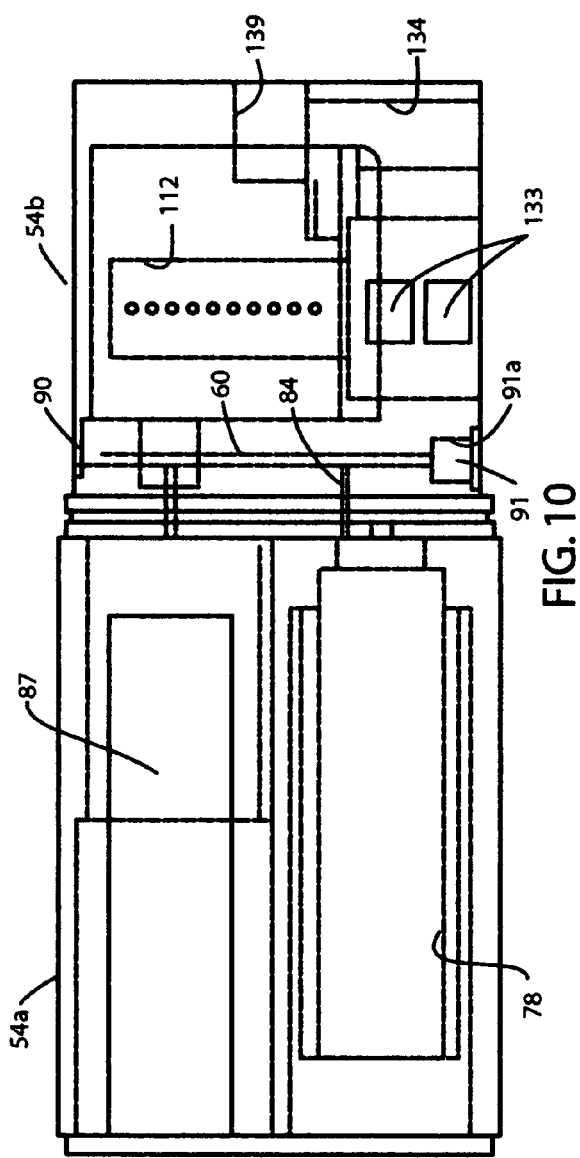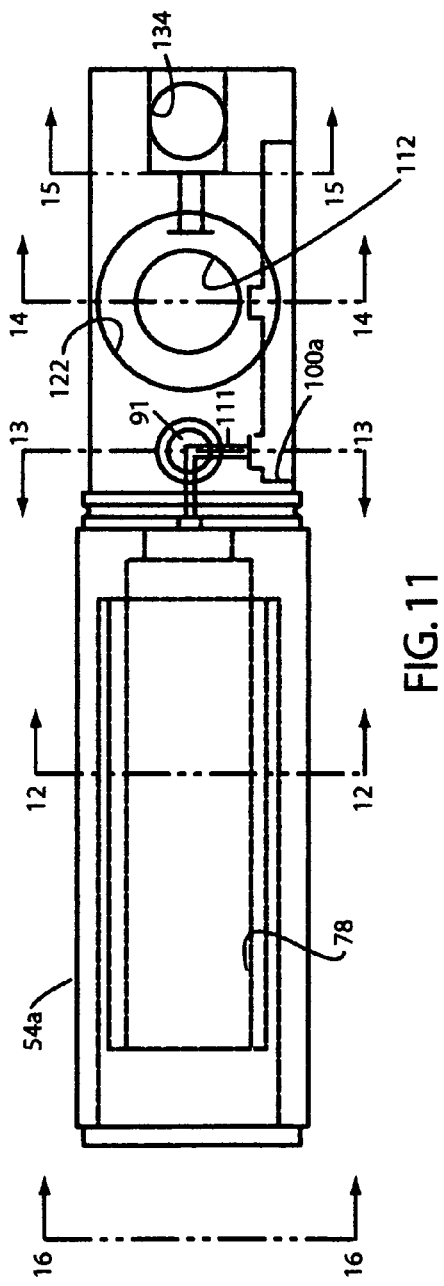
FIG. 10
FIG. 11

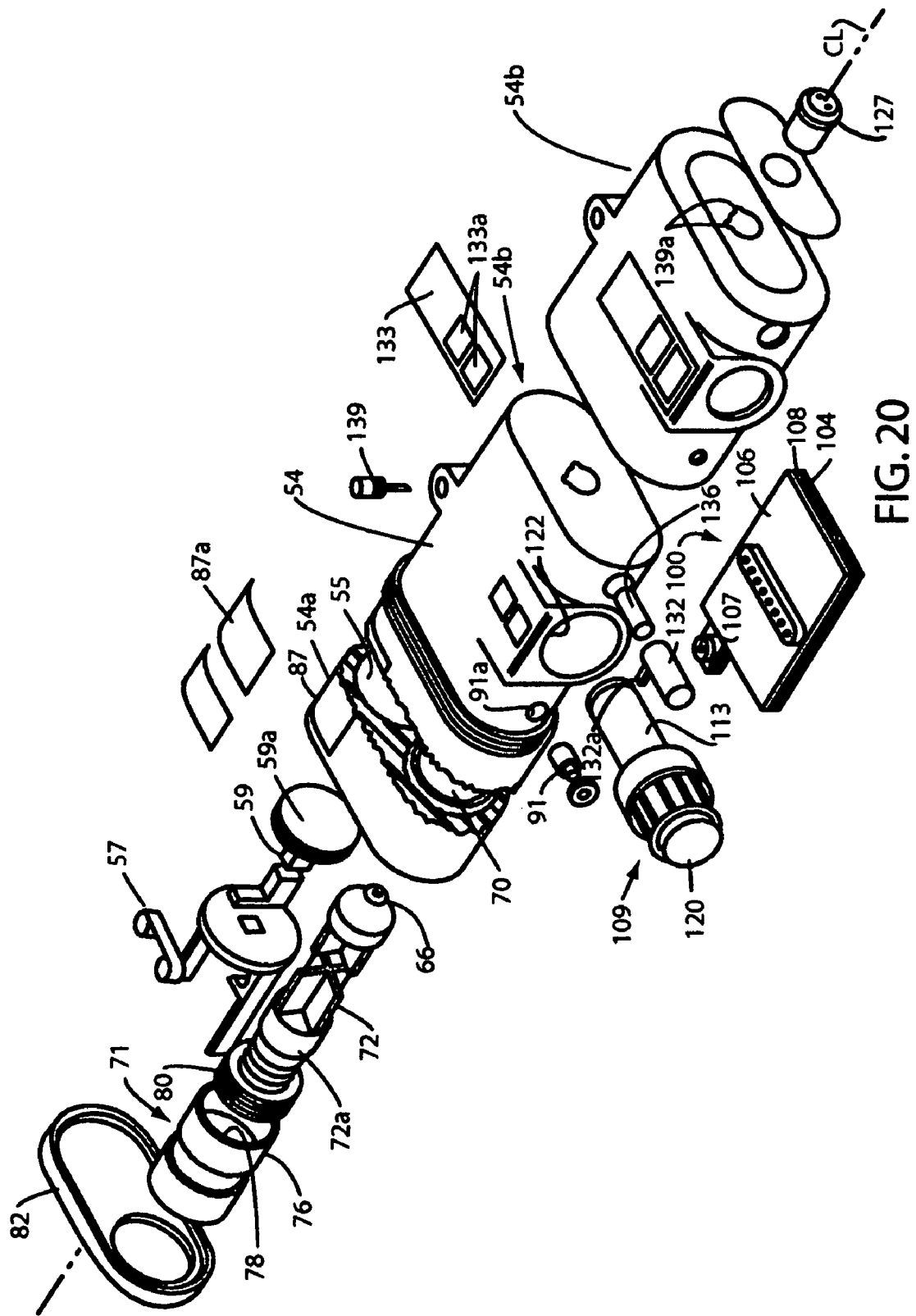

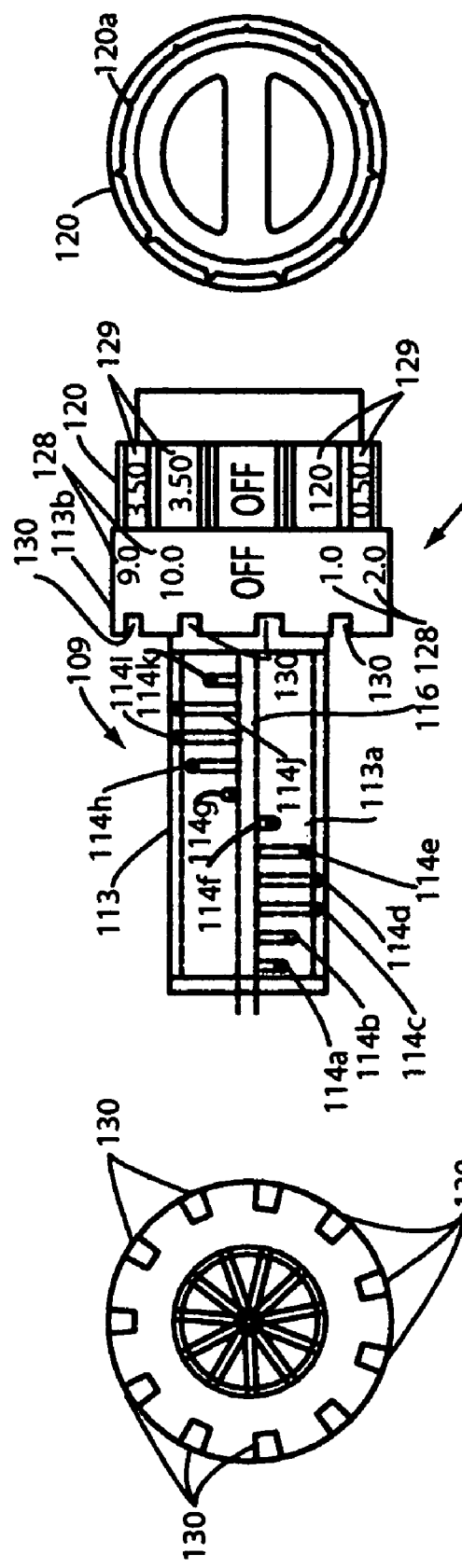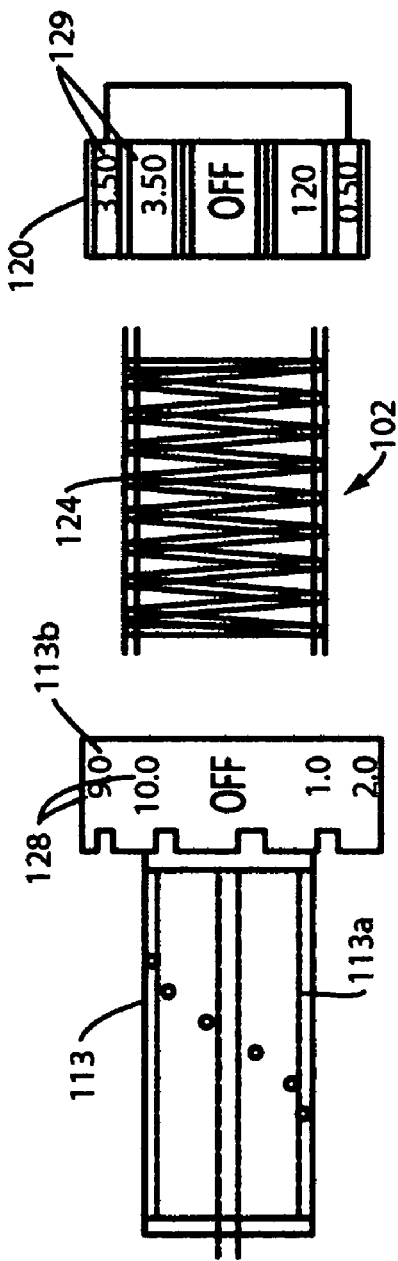

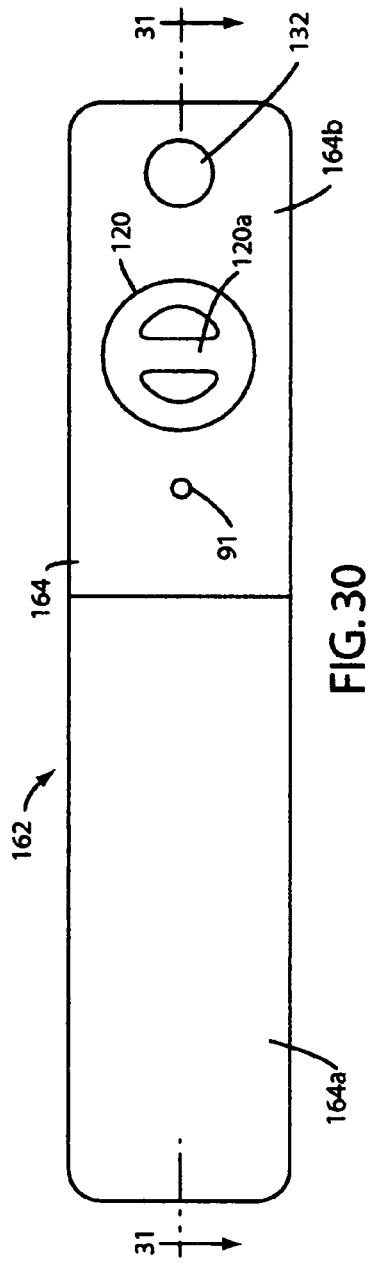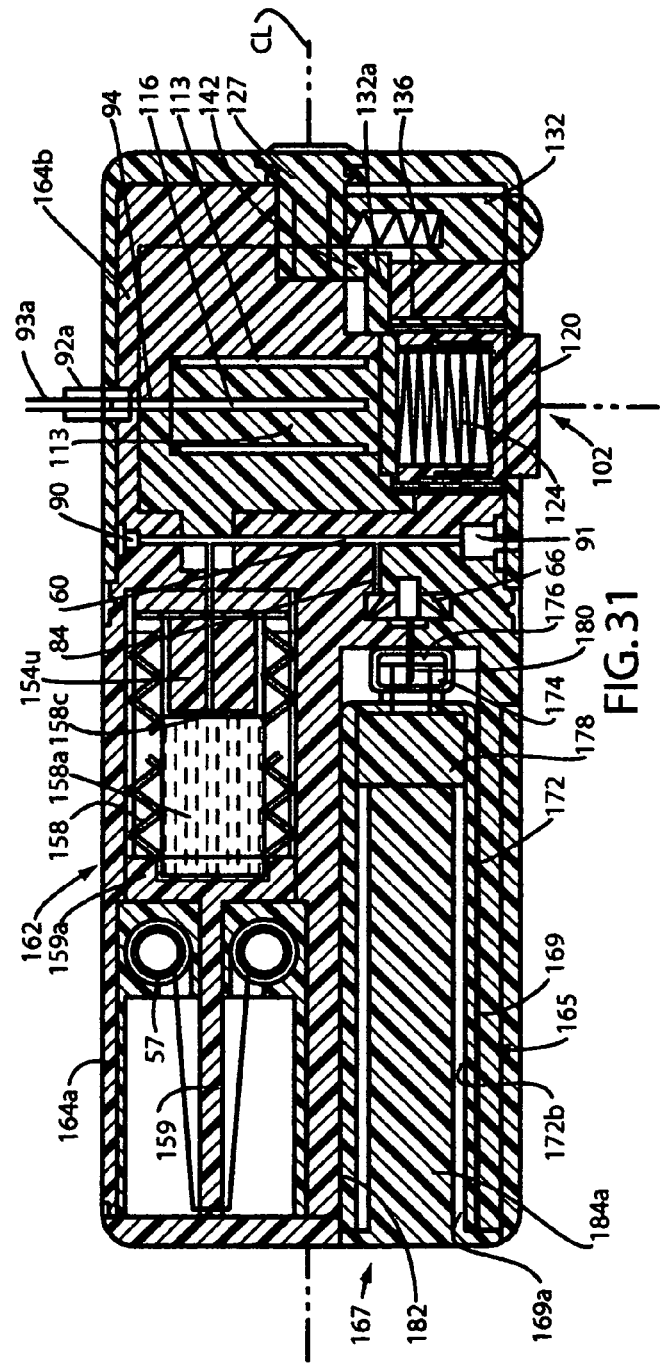

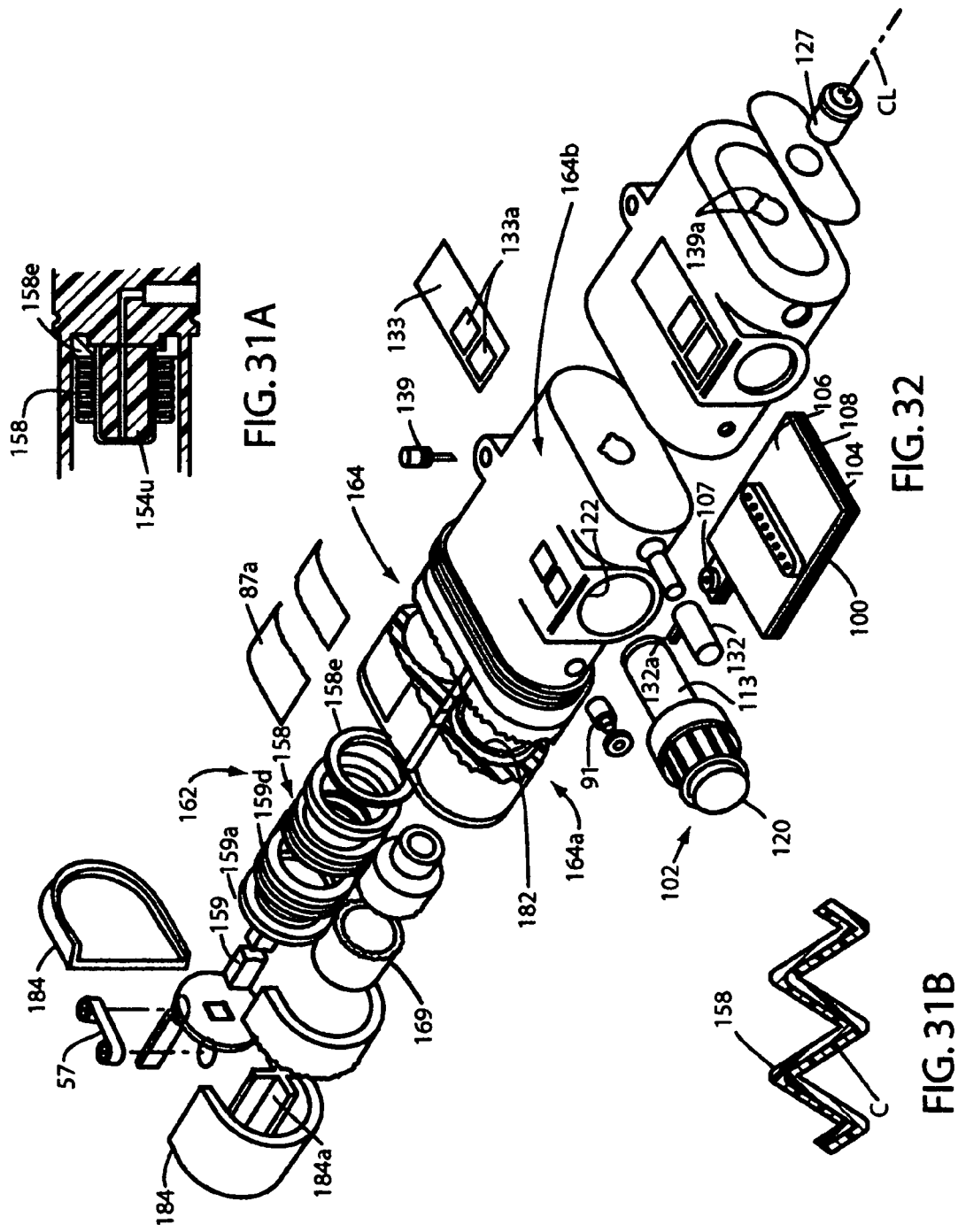

| Channel Type | Flow Rate at 0.5 ATM | Total Channel Length | Cross-sectional Dimensions Width X Depth | Channel Volume | Priming Time at a Pressure of Approximately 0.5 ATM |
|---|---|---|---|---|---|
| Priming channels on the chip | | 8 cm | 1000 μm x 100 μm | .080 ml | |
| Channel in the flow rate selector | | 3 cm | 1000 μm diameter* | .024 ml | |
| Administration line | | 100 cm | 1000 μm diameter* | .785 ml | |
| Priming channel + selector channel + administration line | 0.20 ml/sec | | 40 μm x 100 μm | .89 ml | 4.4 sec |
| 0.1 ml/hr channel | 0.1 ml/hr | 73 cm | 40 μm x 100 μm | $2.9 \times 10^{-3}$ ml | 104.0 sec[1] |
| 0.2 ml/hr channel | 0.2 ml/hr | 36.5 cm | 40 μm x 100 μm | $1.45 \times 10^{-3}$ ml | 25.1 sec |
| 0.3 ml/hr channel | 0.3 ml/hr | 24.3 cm | 40 μm x 100 μm | $9.67 \times 10^{-4}$ ml | 11.6 sec |
| 0.4 ml/hr channel | 0.4 ml/hr | 18.3 cm | 40 μm x 100 μm | $7.32 \times 10^{-4}$ ml | 6.5 sec |
| 0.5 ml/hr channel | 0.5 ml/hr | 14.6 cm | 40 μm x 100 μm | $5.84 \times 10^{-4}$ ml | 4.2 sec[2] |
| 0.6 ml/hr channel | 0.6 ml/hr | 12.2 cm | 40 μm x 100 μm | $4.88 \times 10^{-4}$ ml | 2.9 sec |
| 0.7 ml/hr channel | 0.7 ml/hr | 10.4 cm | 40 μm x 100 μm | $4.16 \times 10^{-4}$ ml | 2.1 sec |
| 0.8 ml/hr channel | 0.8 ml/hr | 9.1 cm | 40 μm x 100 μm | $3.64 \times 10^{-4}$ ml | 1.6 sec |
| 0.9 ml/hr channel | 0.9 ml/hr | 8.1 cm | 40 μm x 100 μm | $3.24 \times 10^{-3}$ ml | 1.3 sec |
| 1.0 ml/hr channel | 1.0 ml/hr | 62.5 cm | 100 μm x 100 μm | $6.25 \times 10^{-3}$ ml | 22.5 sec |
| 2.0 ml/hr channel | 2.0 ml/hr | 31.3 cm | 100 μm x 100 μm | $3.13 \times 10^{-3}$ ml | 5.6 sec |
| 3.0 ml/hr channel | 3.0 ml/hr | 20.8 cm | 100 μm x 100 μm | $2.08 \times 10^{-3}$ ml | 2.5 sec |
| 4.0 ml/hr channel | 4.0 ml/hr | 15.6 cm | 100 μm x 100 μm | $1.56 \times 10^{-3}$ ml | 1.4 sec |
| 5.0 ml/hr channel | 5.0 ml/hr | 12.2 cm | 100 μm x 100 μm | $1.25 \times 10^{-3}$ ml | .9 sec |
| 6.0 ml/hr channel | 6.0 ml/hr | 33.8 cm | 200 μm x 100 μm | $6.76 \times 10^{-3}$ ml | 2.4 sec |
| 10.0 ml/hr channel | 10.0 ml/hr | 35.2 cm | 300 μm x 100 μm | $1.06 \times 10^{-3}$ ml | 3.8 sec |
| 20.0 ml/hr channel | 20.0 ml/hr | 17.6 cm | 300 μm x 100 μm | $5.03 \times 10^{-3}$ ml | 1.0 sec |
| 30.0 ml/hr channel | 30.0 ml/hr | 11.7 cm | 300 μm x 100 μm | $3.53 \times 10^{-3}$ ml | .4 sec |
| 50.0 ml/hr channel | 50.0 ml/hr | 9.9 cm | 400 μm x 100 μm | $3.96 \times 10^{-3}$ ml | 2.9 sec |

FIG. 33

FLUID DELIVERY APPARATUS WITH VIAL FILL

This is a Non-Provisional Application claiming the benefit of co-pending Provisional Application No. 60/654,671 filed Feb. 18, 2005.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which includes novel vial fill means for filling the reservoir of the device and also includes a unique adjustable flow rate control means for precisely adjustably controlling the rate of fluid flow from the reservoir of the device toward the patient.

2. Discussion of the Prior Art

Many medicinal agents require an intravenous route for administration of the medicament. The delivery device for delivering the medicament, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well known in the prior art. Such bladder, or "balloon" type, devices are described in U.S. Pat. No. 3,469,578, issued to Bierman and in U.S. Pat. No. 4,318,400, issued to Perry.

One of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued one of the present inventors, namely U.S. Pat. No. 5,743,879, discloses an injectable medicament dispenser for use in controllably dispensing fluid medicaments such as insulin, anti-infectives, analgesics, oncolylotics, cardiac drugs, biopharmaceuticals, and the like from a pre-filled container at a uniform rate. The dispenser, which is quite dissimilar in construction and operation from that of the present invention, includes a stored energy source in the form of a compressibly deformable, polymeric, elastomeric member that provides the force necessary to controllably discharge the medicament from a pre-filled container, which is housed within the body of the device. After having been deformed, the polymeric, elastomeric member will return to its starting configuration in a highly predictable manner.

Another important prior art fluid delivery device is described in the U.S. Pat. No. 6,063,059 also issued to one of the present inventors. This device is of a completely different construction and embodies a compressible-expandable stored energy source.

As will be appreciated from the discussion which follows, the apparatus of the present invention is uniquely suited to provide precise, continuous fluid delivery management at a low cost in those cases where a variety of precise dosage schemes are of utmost importance. An important aspect of the apparatus of the present invention is the provision of a novel, fluid flow rate control means that includes uniquely formed micro capillary, multichannel flow rate control channels which enable precise control of the rate of fluid flow of the medicament to the patient via a rotatable control knob. More particularly, the apparatus of the present invention includes a novel, adjustable fluid flow rate mechanism which enables the fluid contained within the reservoir of the device to be precisely dispensed at various selected infusion rates.

The apparatus of the present invention can be used with minimal professional assistance in an alternate health care environment, such as the home. By way of example, devices of the invention can be comfortably and conveniently removably affixed to the patient's body or clothing and can be used for the continuous infusion of antibiotics, such as, for example, an injectable antibiotic sold by Abbott Laboratories under the name and style ANCIF and by Rosche under the name and style ROCEPHIN, analgesics, such as morphine and like medicinal agents.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a compressible-expandable spring member that provides the force necessary to substantially, uniformly dispense various solutions from the device reservoir. Because of the simplicity of construction of the apparatus of the invention, and the straightforward nature of the energy source, the apparatus can be manufactured at low cost without in any way sacrificing accuracy and reliability.

SUMMARY OF THE INVENTION

It is an object of the present invention to provide a compact fluid dispenser for use in controllably dispensing fluid medicaments, such as, antibiotics, analgesics, and like medicinal agents from the reservoir of the device.

It is another object of the invention to provide a fluid dispenser of the aforementioned character, which is highly reliable and is easy-to-use by laypersons in a non-hospital environment.

Another object of the invention is to provide a small, compact fluid dispenser that includes a novel bellows-type reservoir and vial fill means for filling the bellows-type dispenser reservoir with the medicament to be dispensed.

Another object of the invention is to provide an apparatus which can be factory pre-filled with a wide variety of medicinal fluids or one which can readily be filled in the field shortly prior to use.

Another object of the invention is to provide a dispenser in which a stored energy source which controllably urges the medicinal fluid from the device reservoir is provided in the form of a constant force spring member of novel design that provides the force necessary to continuously and substantially uniformly expel fluid from the device reservoir.

Another object of the invention is to provide a device of the aforementioned character which includes novel adjustable flow rate control means disposed intermediate the fluid reservoir outlet and the outlet port of the device for precisely controlling the rate of fluid flow from the outlet port toward the patient.

Another object of the invention is to provide a device as described in the preceding paragraph in which the flow rate control means comprises a rate selector member for selecting the desired rate of fluid flow toward the patient and a cooperatively associated flow rate control assembly that includes a unique flow control plate having a plurality of fluidic microchannels which controls the rate of fluid flow toward the selector member.

Another object of the invention is to provide a device of the character described which includes priming means for priming the various fluid passageways of the device and purging the fluid passageways of gases that may be contained therein prior to the delivery of the medicinal fluids to the administration line of the device. More particularly, an object of the invention is to provide such a device in which the flow control plate of the flow rate control means is provided with a priming channel that is in communication with the plurality of elongated fluidic flow control channels formed in a rate control plate and is also in communication with the rate selector member that is rotatably carried by the device housing.

Another object of the invention is to provide a fluid dispenser of the class described which is compact, is lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir.

Another object of the invention is to provide a self-contained medicament dispenser which is of very simple construction and yet extremely reliable in use.

Another object of the invention is to provide a fluid dispenser as described in the preceding paragraphs, which is easy and inexpensive to manufacture in large quantities.

BRIEF DESCRIPTION OF THE DRAWINGS

FIG. 2 is a top plan view of the fluid dispensing device shown in FIG. 1.

FIG. 3 is an end-view of the fluid dispensing device shown in FIGS. 1 and 2.

FIG. 4 is a cross-sectional view taken along lines 4-4 of FIG. 2.

FIG. 5 is a cross-sectional view taken along lines 5-5 of FIG. 2.

FIG. 8 is a side view of the fluid dispensing device shown in FIG. 1.

FIG. 9 is a cross-sectional view taken along lines 9-9 of FIG. 8.

FIG. 10 is a top plan view of the housing of the device showing internal construction in dotted lines.

FIG. 11 is a side-elevational view of the housing of the device showing some internal construction in dotted lines.

FIG. 20 is a generally perspective, exploded view of the fluid dispensing device of the form of the invention shown in FIG. 1.

FIG. 23 is an enlarged view of the selector assembly of the invention shown in the upper portion of FIG. 21.

FIG. 24 is a left-end view of the selector assembly shown in FIG. 23.

FIG. 25 is a right-end view of the selector assembly shown in FIG. 23.

FIG. 26 is a generally perspective, exploded view of the selector assembly shown in FIG. 23.

FIG. 30 is a side view of yet another form of the fluid dispensing device of the present invention.

FIG. 31 is a cross-sectional view taken along lines 31-31 of FIG. 30.

FIG. 31A is a fragmentary cross-sectional view of a portion of the bellows structure of the apparatus of the invention.

FIG. 31B is a greatly enlarged, cross-sectional view of a portion of the side wall of the bellows reservoir of one form of the invention.

FIG. 32 is a generally perspective, exploded view of the fluid dispensing device of the form of the invention shown in FIG. 30.

FIG. 33 is a generally tabular view illustrating the fluidic properties of one form of the fluid rate control member, or rate control chip, of the form of the flow rate control device shown in FIG. 22.

DESCRIPTION OF THE INVENTION

Figure 6:
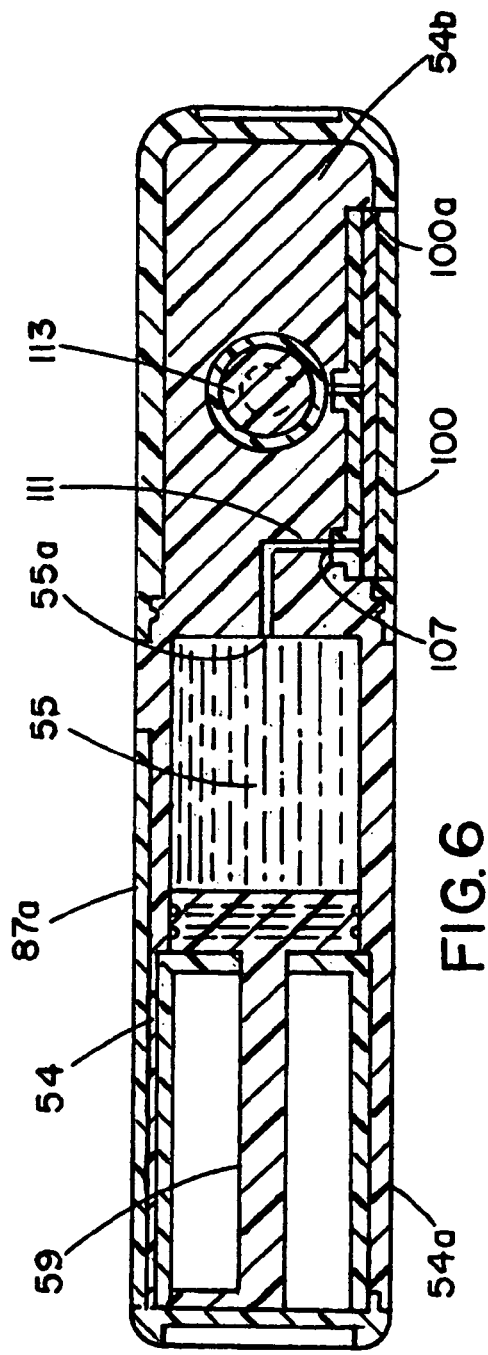
FIG. 6 is a cross-sectional view taken along lines 6-6 of FIG. 2.

Referring to the drawings and particularly to FIGS. 1 through 23, one form of the fluid dispensing device of the present invention is there shown and generally designated by the numeral 52. As best seen in FIGS. 9 and 20, the apparatus here comprises a snap-together outer housing 54 having an axial centerline "CL" and first and second portions 54a and 54b respectively. Housing portion 54a houses the reservoir portion and the reservoir-fill portion, while housing portion 54b houses the flow control, the fluid delivery and the control portions of the apparatus. Disposed within first portion 54a of outer housing 54 and on one side of the axial centerline is a fluid reservoir 55 (FIGS. 4, 6 and 9). Fluid reservoir 55 is provided with an inlet-outlet passageway 55a for permitting fluid flow into and out of the fluid reservoir (FIG. 9).

Also disposed within first portion 54a of outer housing 54 on one side of the axial centerline CL is the novel stored energy means of the invention for acting upon the fluid contained within fluid reservoir 55 in a manner to cause the fluid contained therewithin to controllably flow outwardly of the reservoir, through the flow control means of the invention and onwardly toward the patient. In the present form of the invention, this important stored energy means comprises a constant force spring member 57 that is carried within first portion 54a of the outer housing. Spring member 57 is first extended by fluid flowing into reservoir 55 and then controllably retracts to cause fluid flow from the fluid reservoir 55 through the flow control means of the invention.

Stored energy member or constant force spring 57, which is a special variety of spring, is readily commercially available from several sources, including Barnes Group Inc. of Bristol, CT, stock Drive Products/Sterling Instrument of Hyde Park, NY and Walker Corporation of Ontario, Canada. Constant force extension spring 57 is basically a high stress, long deflection device that offers great advantages when used in applications where very low or zero gradient is desired, where space is a factor and where very high reliability is required. Constant force springs, such as spring 57, provide markedly superior constant force loading when compared to conventional helical extension or like springs. Spring 57, after being expanded, tends to uniformly return toward its starting configuration and in so doing will exert an inward pressure on a pusher means, shown here as pusher member 59 of the character shown in FIG. 9 Pusher member 59 functions to act on the fluid within the fluid reservoir 55 in a manner to cause the fluid contained within the reservoir to flow outwardly thereof through outlet 55a and toward the flow rate control means of the invention at a substantially constant rate. As clearly illustrated in FIGS. 9, 28 and 29 spring 57 has two spaced apart coiled portions that are located on either side of the pusher member 59. The coiled portions are interconnected by an elongated strip portion that engages the pusher member. For certain applications the inner surfaces of reservoir 55 and the front surface of pusher member 59 can be coated for drug and environmental compatibility.

Forming an important aspect of the apparatus is the fill means of the apparatus, which is also carried by the first portion 54a of outer housing 54 on the opposite side of the axial centerline "CL" from that of the stored energy means. This important fill means functions to controllably fill the reservoir 55 with the fluid to be dispensed. As best seen in FIG. 9, housing portion 54a includes a fluid passageway 60 that communicates with inlet 55a of fluid reservoir. Fluid passageway 60 also communicates with a cavity 64 formed within first portion 54a of the housing. Disposed within cavity 64 is a conventional, umbrella-type check valve 66, which permits fluid flow toward fill passageway 60, but blocks fluid flow in the opposite direction. Passageway 60 also communicates, via check valve 66, with a chamber 70 which comprises a part of one form of the fill means of the invention.

Chamber 70 is constructed and arranged to telescopically receive the medicament fill vial assembly portion 71 of the fill means of the invention, the character of which will presently be described. An elongated support 72, which is mounted within chamber 70 includes a threaded end portion 72a and carries an elongated, longitudinally extending, hollow needle 74 having a central fluid flow passageway.

Figure 7:
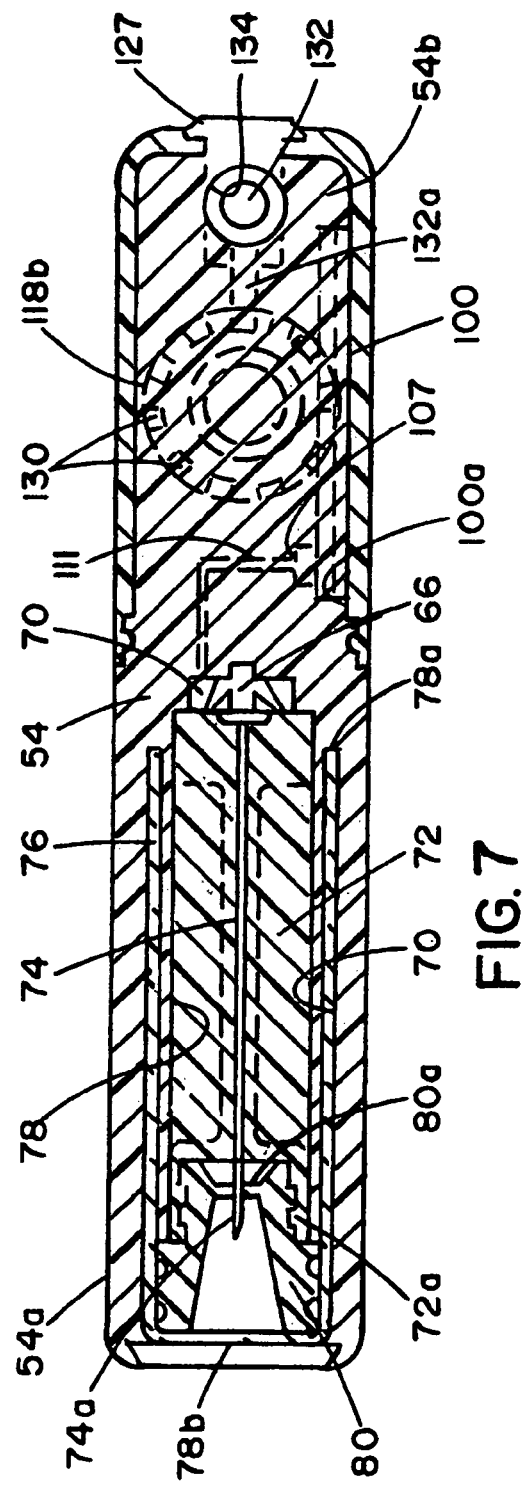
FIG. 7 is a cross-sectional view taken along lines 7-7 of FIG. 2.

Referring particularly to FIGS. 7 and 9, the medicament containing fill vial assembly 71 here includes a fill vial 76 having a fluid chamber 78 for containing the injectable fluid medicament. Chamber 78 is provided with a first open end 78a and second closed end 78b. First open end 78a is sealably closed by closure means here provided in the form of an externally threaded elastomeric plunger 80, which is telescopically movable within chamber 78 from a first location where the plunger is disposed proximate first open end 78a to the second, device-fill location where the plunger is disposed proximate second closed end 78b (FIGS. 7 and 9).

After removal of closure cap 82 from housing portion 54a (FIG. 20), vial assembly 71 can be introduced into chamber 78 (FIGS. 7 and 9) thereby placing chamber 78 in fluid communication with hollow needle 74. As the fill vial assembly is so introduced and the plunger 80 is threadably interconnected with threaded end of elongated support 72, the sharp end 74a of the elongated needle 74 will pierce the central wall 80a of the elastomeric plunger in the manner shown in FIGS. 7 and 9. An inward pressure exerted on the vial assembly will cause the vial to move inwardly of chamber 78 and will cause the structural support 72 to move the elastomeric plunger inwardly of the vial chamber 78 in a direction toward the second or closed end 78b of the vial chamber. As the plunger is moved inwardly of the vial container, the fluid contained within the vial chamber will be expelled therefrom into the hollow elongated needle 74 having a sharp end, which has pierced the central wall 80a of the elastomeric plunger. The fluid will then flow past conventional umbrella-type check valve 66, into a fluid passageway 84 formed in the device housing and thence into a fluid passageway 60 which communicates with reservoir inlet 55a.

Figure 1:
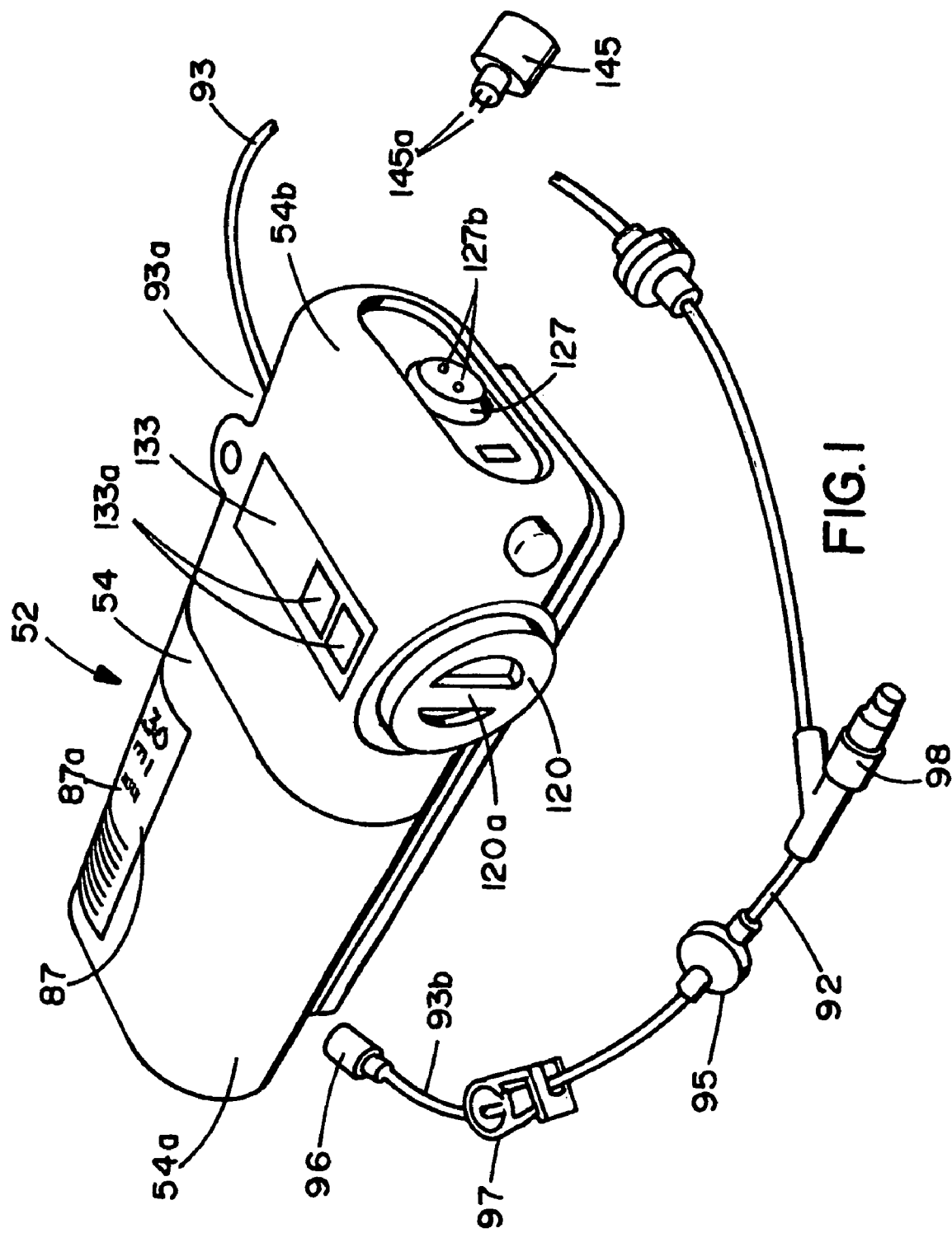
FIG. 1 is a generally perspective view of one form of the fluid dispensing device of the present invention.

As the fluid flows into reservoir 55, it will exert a rearward pressure on the plunger end portion 59a of pusher member 59 causing it to move rearwardly. As the pusher member moves rearwardly, it will exert forces on spring member 57 causing it to expand from its retracted configuration to its extended configuration shown in FIG. 9. This rearward movement of pusher member can be viewed through a volume indicator window 87 and tracked by a volume indicator 87a which indicates that the reservoir has changed from an empty configuration to a filled configuration (FIG. 1).

As the reservoir 55 fills with fluid, any gases trapped within the reservoir will be vented to atmosphere via vent means "V" mounted in portion 54b of the housing. This vent means here comprises a gas vent 90 that can be constructed of a suitable hydrophobic porous material such as a porous plastic.

An alternate form of fill means is also provided in this first embodiment of the invention. This alternate fill means comprises a pierceable septum 91 that is mounted within a cavity 91a provided in housing portion 54b. Septum 91 is pierceable by the needle of a conventional syringe that is filled with the beneficial agent to be dispensed to the patient (not shown). As shown in FIG. 9, cavity 91a is in communication with passageway 60 so that the beneficial agent contained within the syringe can flow under pressure from the pierced septum directly into fluid reservoir 55 to cause the spring 57 to extend in the manner shown in FIG. 9.

Upon opening the fluid delivery path to the fluid delivery means of the invention, shown here as a conventional administration set 92 (FIG. 1), the stored energy means, or spring 57, will tend to return to its starting configuration thereby controllably urging fluid flow outwardly of reservoir 55 and toward the administration set via the flow control means of the invention the character of which will presently be described.

Administration set 92 is connected to the second portion 54b of housing 54 by a connector 92a in the manner shown in FIG. 9 of the drawings. The proximal end 93a of administration line 93 of the administration set is in communication with an outlet fluid passageway 94 which is formed in housing portion 54b in the manner best seen in FIG. 9. Disposed between the proximal end 93a and the distal end 93b of the administration line is a conventional gas vent and filter 95. Provided at the distal end 93b is a luer connector 96 of conventional construction (FIG. 1). Between gas vent and filter 95 and luer connector 96 is a conventional line clamp 97 and disposed between gas vent and filter 95 and the proximal end 93a of the administration line is a conventional "Y" site 98.

A number of beneficial agents can be contained within the fill syringe or the vial used to fill reservoir 55 and can be controllably dispensed to the patient including, by way of examples, medicaments of various types, drugs, pharmaceuticals, hormones, antibodies, biologically active materials, elements, chemical compounds, or any other suitable material useful in diagnostic cure, medication, treatment or prevention of diseases or the maintenance of the good health of the patient.

As the fluid contained within reservoir 55 is urged outwardly thereof by the stored energy means, the fluid will flow under pressure through reservoir outlet 55a (FIG. 9) and then on toward the flow control means of this latest form of the invention. This important flow control means functions to precisely control the rate of fluid flow flowing from the reservoir 55 toward the patient.

Figure 22:
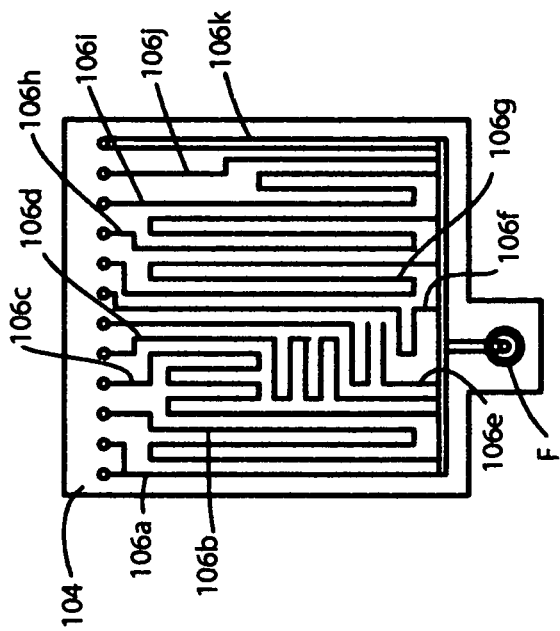
FIG. 22 is a top plan view of one form of the rate control plate or member shown in FIG. 21.
Figure 21:
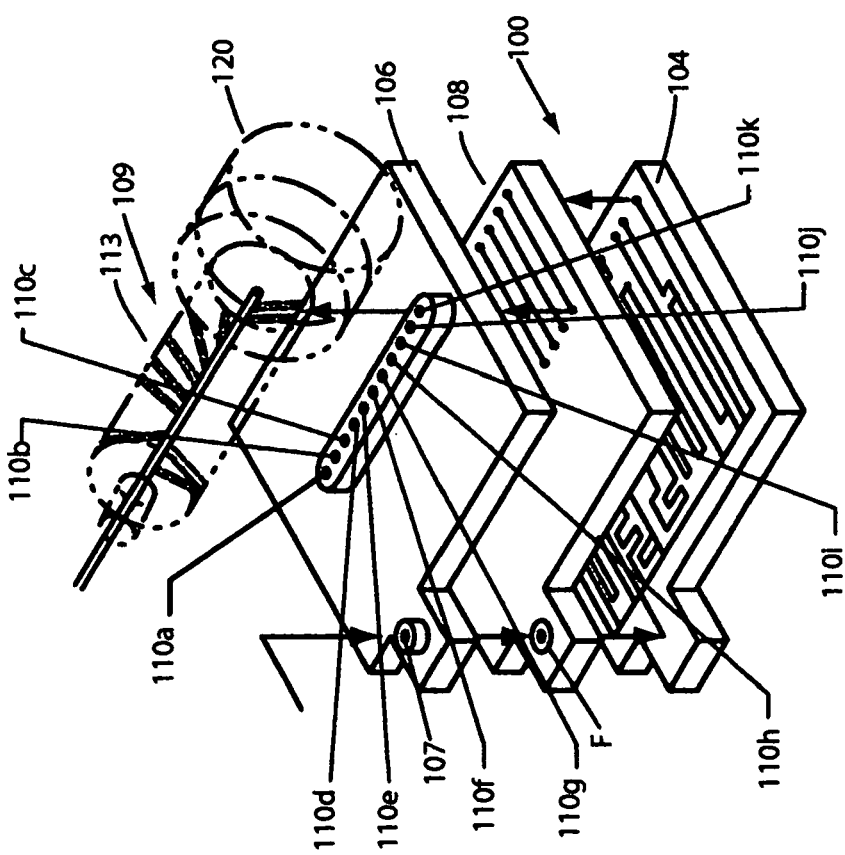
FIG. 21 is a generally perspective, exploded view of the flow rate control assembly of the fluid dispensing device shown in FIG. 1.

Referring to FIGS. 9 and 20 through 26, it can be seen that the flow rate control means of the flow control means of this latest form of the invention comprises a rate control assembly 100 (FIG. 21) and a selector means, or selector assembly 102 (FIGS. 23 and 26). Rate control assembly 100 is mounted within a cavity 100a formed in housing portion 54b (FIGS. 6, 7, 14 and 15) and includes a base plate, or rate control member 104, a cover member 106 and a distribution plate 108 disposed between members 104 and 106 (FIG. 21). Cover member 106 is provided with a fluid inlet port 107 and a plurality of spaced-apart fluid outlet ports 110a, 110b, 110c, 110d, 110e, 110f, 110g, 110h, 110i, 110j and 110k respectively. As illustrated in FIG. 22, flow rate control member, or base plate, 104 is uniquely provided with a plurality of micro rate flow control channels 106a, 106b, 106c, 106d, 106e, 106f, 106g, 106h, 106i, 106j and 160k respectively, each having an inlet and an outlet. As indicated in the drawings, the outlets of the micro rate flow control channels are in communication with the spaced-apart outlet ports of the cover member 106 via the various flow passageways formed in distribution plate 108 and the inlet port is in fluid communication with reservoir 55 via a passageway 111 (FIG. 7) as indicated by the arrows of FIG. 21.

Before further discussion of the operation of the selector means of the invention, the details of the construction of the rate control plate 80 and the various methods of making the rate control plate will now be considered. With respect to materials, the most appropriate materials for constructing the rate control plate are medical grade polymers. These types of polymers include thermoplastics, duroplastics, elastomers, polyurethanes, acrylics and epoxies. In other variations, the materials used for the flow control plate may be made of glass or silica. In further variations, the flow control component may be made of metals or inorganic oxides.

Using the foregoing materials, there are several ways that the flow control channels can be made. These include injection molding, injection-compression molding, hot embossing, laser ablation and casting. The techniques used to make these imbedded fluid channels are now commonplace in the field of microfluidics, which gave rise to the lab-on-a-chip, bio-MEMS and micro-total analysis systems (μ-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 μm. Subsequently, electroforming is performed to produce the negative metal form, or mold insert. Alternatively for larger channel systems, precision milling can be used to make the mold die insert directly. Typical materials for the mold insert or embossing tool are nickel, nickel alloys, steel and brass. Once the mold insert or embossing tool is fabricated, the polymer of choice may be injection molded or embossed to yield the desired part with imprinted channels.

Figure 22A:
FIG. 22A is a greatly enlarged, cross-sectional view of one of the fluidic micro channels of the flow control means of the invention.

Alternatively, channels can be made by one of a variety of casting processes. In general, a liquid plastic resin, for example, a photopolymer, can be applied to the surface of a metal master made by the techniques described in the preceding paragraph and then cured via thermal or ultraviolet (UV) means. After hardening, the material is then "released" from the mold to yield the desired part. Additionally, there are similar techniques available that utilize CAD data of the desired channel configuration and direct laser curing of a liquid monomer to yield a polymerized and solidified part with imbedded channels. This process is available by contract, from, by way of example, MicroTEC, GmbH of Duisburg, Germany. As shown in FIG. 22A, for certain applications, the surfaces of the channels, such as channel 106a, can be modified as at "M" to provide unique characteristics for purposes of drug compatibility and other environmental considerations.

In order to seal the flow control channels, a planar top plate may be used. In this instance, the channel system may be sealed with a top plate, which is here defined as any type of suitable cover that functions to seal the channel. The top plate may be sealably interconnected with the base plate which contains the flow channels by several means, including thermal bonding, sonic welding, laser welding, adhesive bonding and vacuum application.

Thermal bonding may be performed by using a channel base plate material and planar top cover that are made of similar polymeric materials. In this case, the two substrates are placed in contact with one another, confined mechanically and heated to 2-5° C. above their glass transition temperature. Following a holding period sufficient enough for the polymer molecules of the two surfaces to interpenetrate with one another, the temperature is slowly reduced and a stress-free bonded interface with imbedded micro-channels is yielded.

Additionally, the top plate may be bonded to the base plate through the use of one or more suitable bonding materials or adhesives. The bonding material or adhesive may be of the thermo-melting variety or of the liquid or light curable variety. For thermo-melting adhesives, the adhesive material is melted into the two apposed surfaces, thereby interpenetrating these surfaces and creating a sealed channel structure.

Further, liquid curable bonding materials or adhesives and light curable bonding materials or adhesives may be applied to one of the surfaces, for example the top plate. Subsequently, the other surface is brought into contact with the coated surface and the adhesive is cured by air exposure or via irradiation with a light source. Liquid curable bonding materials or adhesives may be elastomeric, for example, thermoplastic elastomers, natural or synthetic rubbers, polyurethanes, and silicones. Elastomeric bonding materials may or may not require pressure to seal the channel system. They may also provide closure and sealing to small irregularities in the apposed surfaces of the channel system.

A channel system may also be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

While the rate control plate can be constructed in various sizes, a rate control chip which is rectangular in shape and approximately 11 cm long and approximately 5 cm wide is suitable for the present application. Similarly, while the depth of the channels can vary depending upon the end-use of the device, as a general rule the depth of the channels is on the order of approximately 1-1000 μm.

As previously mentioned, the cross section of the set of channels may vary in area over the members of the set of individual channels so as to achieve the specified flow rate of a particular channel. The cross section may also vary over the length of any particular channel so as to achieve the specified flow rate for the particular channel. Some examples of typical channel cross sections are square, rectangular, elliptical, circular, semi-circular and semi-elliptical. Channel cross sections may also be more complicated than those noted explicitly here.

A typical chip will be able to deliver fluid at five specified flow rates as, for example 0.25, 0.5, 1.0, 2.0 and 5.0 ml/hr. and greater for optimum performance, the flow rate should be constant and within 10% of the desired specified value at room temperature.

In operation, the flow through the flow control channels is controlled by taking advantage of the viscous drag imposed on the moving fluid by the walls of the channels. For a given imposed pressure and channel cross section, the longer the channel the smaller the flow rate. The pressure required to achieve the desired flow rates in the micron channels is preferably in the range of from 0.01 to 1 ATM. However, for some applications it may be desirable to exceed these limits.

The path that the micro-channels take in any given rate control plate may be straight, a single meander or two or more meanders or serpentines. The turns of the meanders may be of any angle from approximately 45° to approximately 220°. The runs of straight path between turns of the meanders may be of any length that the chip can accommodate, but these straight runs would typically be from 50 μm to 500 82 m in length.

Considering now the important selector means of the invention for selecting the rate of fluid flow to the patient, as best seen by referring to FIGS. 23 through 26, the selector means of this form of the invention includes a selector assembly 109, which comprises a selector member 113 that is carried within a transverse bore 112 formed in housing portion 54b (FIG. 9). Selector member 113 includes a body portion 113a and an enlarged diameter head portion 113b. As illustrated in FIGS. 23 and 24, body portion 113a is uniquely provided with a plurality of radially-extending flow control channels 114a, 114b, 114c, 114d, 114e, 114f, 114g, 114h, 114i, 114j and 114k, each having an inlet port and an outlet port which is in fluid communication with an axially-extending passageway 116. Axially-extending passageway 116 is, in turn, in fluid communication with administration line 93a via passageway 94 (FIG. 9). In a manner presently to be described, selector assembly 109 functions to selectively align one of the inlets of the radially-extending flow control channels of selector member 113 with a selected one of the spaced-apart fluid outlet ports 110a, 110b, 110c, 110d, 110e, 110f, 110g, 110h, 110i, 110j and 110k of the rate control cover 106 (FIG. 21).

Selector member 113 has an axial center line "CL-S" that extends substantially perpendicular to the axial center-line "CL" of housing 54. As illustrated in FIGS. 23 and 26, the selector means, in addition to selector member 113, also includes a cooperating control knob 120, which is used to controllably rotate selector member 113.

Another important feature of the present invention resides in the provision of locking means for locking the selector member 113 in position after a particular fluid flow microchannel has been selected through rotation of a selector knob 120, which is maintained in operable association with head portion 113b by means of a coil spring 124 (FIGS. 9 and 26). This important locking means of the invention here comprises a release means or plunger assembly 126 and an operably associated, physician key operated, key lock member 127 (FIG. 9).

Figure 9A:
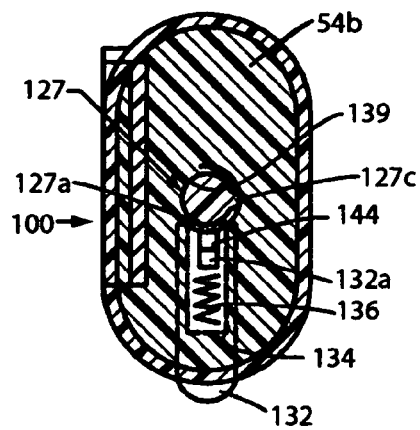
FIG. 9A is a cross-sectional view taken along lines 9A-9A of FIG. 9.

As indicated in FIGS. 23 and 24, head portion 113b of selector member 113 is provided with fluid flow volume indicating indicia 128, while selector knob 120 is provided with flow rate indicating indicia 129. These indicating indicia are viewable through windows 133a formed in a viewing plate 133 carried by housing 54b (see FIG. 20). The head portion 113b of selector member 113 is also provided a plurality of circumferentially-spaced-apart indexing cavities 130. Cavities 130 are adapted to receive the end of the outwardly-extending finger portion 132a of a locking member 132 that is carried within a bore 134 formed in housing portion 54b. Locking member 132 is movable inwardly of housing portion 54b against the urging of locking member biasing means, or spring 136, which is carried within a bore 137 formed in locking member 132. Referring to FIGS. 9 and 9A, it is to be observed that when the key lock member has been rotated within bore 139, within which it is rotatably mounted, to the release position shown in FIG. 9A, locking member 132 is movable within housing portion 54b between the first locked position shown in FIG. 9 and the second inward release position wherein selector member 113 can be freely rotated to an alternate selected position.

Figure 9B:
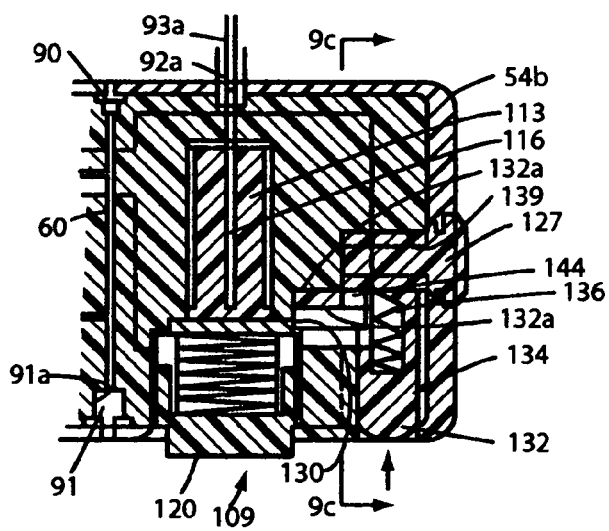
FIG. 9B is a fragmentary cross-sectional view of the forward portion of the apparatus showing the locking means moved into a release position.
Figure 9C:
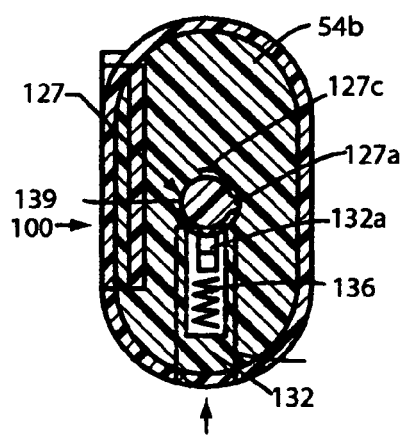
FIG. 9C is a cross-sectional view taken along lines 9C-9C of FIG. 9B.
Figure 12:
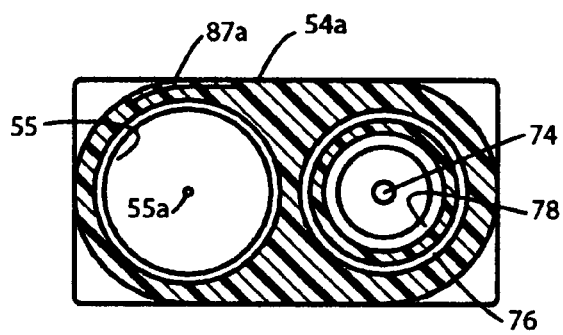
FIG. 12 is a cross-sectional view taken along lines 12-12 of FIG. 11.
Figure 13:
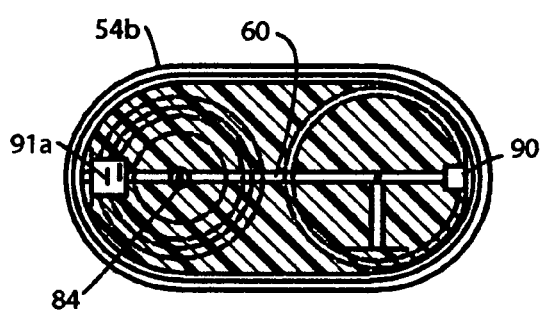
FIG. 13 is a cross-sectional view taken along lines 13-13 of FIG. 11.
Figure 14:
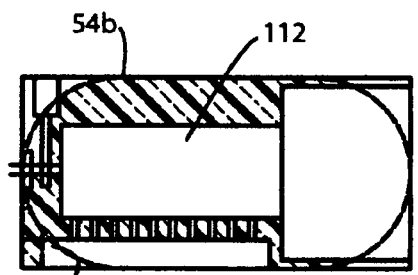
FIG. 14 is a cross-sectional view taken along lines 14-14 of FIG. 11.

As indicated in FIGS. 9 and 9A, when the key lock member 127 is in the position there shown, inward movement of locking member 132 is prevented due to an extension 142 formed on finger portion 132a of locking member 132 engaging a protrusion 127a formed on the shank portion of key lock member 127. However, when the key lock member is rotated within bore 139 by means of a physician's key 145 (FIG. 1) to the second position shown in FIG. 9C protrusion 127a is rotated 90 degrees so that extension 142 is free to move inwardly in the manner shown in FIGS. 9B and 9C. With this construction, as locking member 132 is moved inwardly against the urging of spring 136, extension 142 will also move inwardly a sufficient distance so that locking member 132 will move out of the cavity 130 of head portion 113b within which it was located. This will permit free rotation of selector member 113 by selector knob 120 in a manner to bring another of the radial fluid flow passageways formed within the selector member into index with a selected one of the outlet ports formed in cover member 106. As shown in FIG.

25, selector knob 120 is provided with a cross bar 120a to assist in its rotation. When the selector member 113 has been rotated into the selected flow rate position, inward pressure on locking member 132 is released causing finger portion 132a to move into locking engagement with another of the cavities 130 formed and the head portion 113b of selector member 113. Key lock member 127 is then rotated to its initial position shown in FIGS. 9 and 9A to once again prevent further rotation of the selector member 113 until the physician, or caregiver in possession of the physician's key once again rotates the key lock member of the locking means into a release position. With the selector member 113 in this alternate, locked position, fluid will flow from the device reservoir through the micro-channel that is communicating with the selected outlet port and then onward toward the administration set at a precise rate of the flow. As indicated in FIG. 21, fluid flowing from the device reservoir will be filtered by filter means shown here as a filter "F" before flowing toward the fluidic micro channels.

Figure 15:
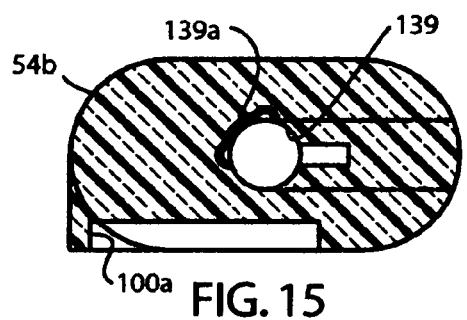
FIG. 15 is a cross-sectional view taken along lines 15-15 of FIG. 11.
Figure 16:
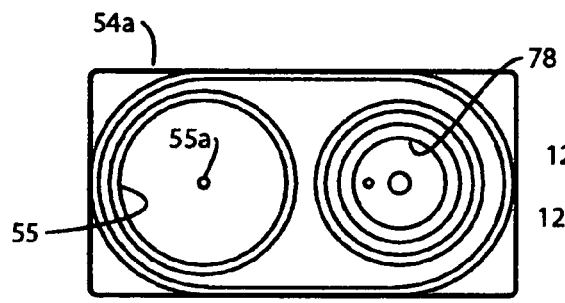
FIG. 16 is a view taken along lines 16-16 of FIG. 11.
Figure 18:
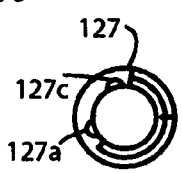
FIG. 18 is a left-end view of the rate control knob shown in FIG. 17.
Figure 17:
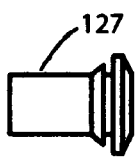
FIG. 17 side-elevational view of one form of the rate control knob of the apparatus of the invention.
Figure 19:
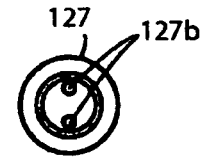
FIG. 19 is a right-end view of the rate control not shown in FIG. 17.

As can be seen by referring to FIGS. 1 and 19, the head portion of key lock member 127 is provided with spaced-apart tang receiving apertures 127b which closely receive tangs 145a provided on the physician's key 145, which is of the general configuration shown in FIG. 1 of the drawings. By inserting the tangs 145a of the physician's key into the apertures 127b formed in the key lock member, the key lock member can be rotated from the locked position shown in FIG. 9 to the release position shown in FIG. 9A. As illustrated in FIGS. 15 and 18, bore 139, within which the key lock member rotates, is provided with circumferentially-spaced-apart cavities 139a that closely receive circumferentially-spaced-apart protuberances 127a and 127c formed on key lock member 127 (FIG. 18) when the key lock member is rotated between the locked and release positions. These cavities and protuberances cooperate to ensure that when the key lock member is rotated into the release position, extension 142 formed on finger 132a is free to move inwardly to the release position shown in FIGS. 9B and 9C. The protuberances 127a and 127c further function to provide a tactile indication that the key locked member has then moved into the release position.

Through appropriate manipulation of the locking means of the invention and the control knob 120 in the manner previously described, it is apparent that the caregiver can select the desired rate of fluid flow from reservoir 55 to the patient. Further, it is to be noted that the selected rate of fluid flow to the patient cannot be altered by anyone other than the physician or caregiver having possession of the physician's key.

The apparatus of this latest form of the invention also includes disabling means for irrevocably disabling the device and rendering it inert. Referring to FIGS. 5 and 9, this disabling means here comprises a disabling shaft 135 that is telescopically movable within a passageway 137 formed within housing portion 54b. As best seen in FIG. 5, shaft 135 has a distal end 135a, which, upon insertion of the shaft distal end into passageway 95, will block fluid flow through the passageway. A friction-fit retainer 135a normally holds shaft 135 in the retracted position.

Figure 27:
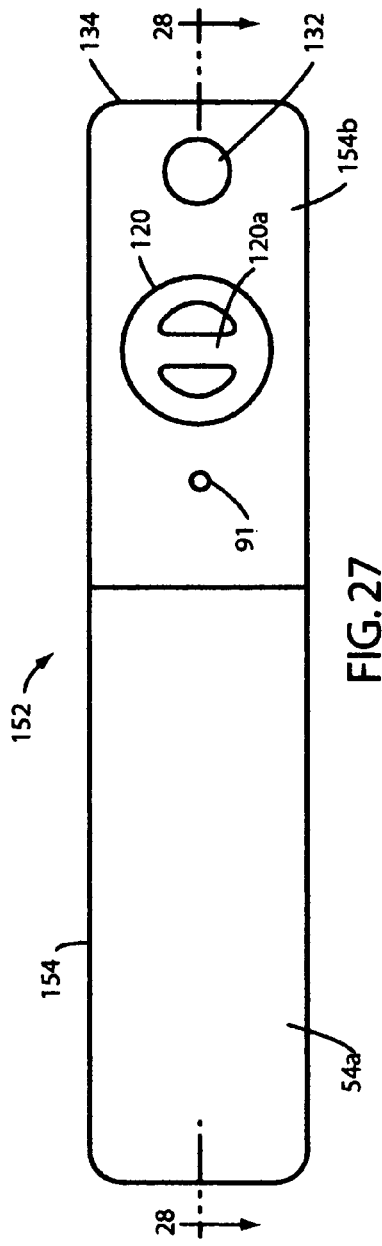
FIG. 27 is a side view of still another form of the fluid dispensing device of the present invention.
Figure 28:
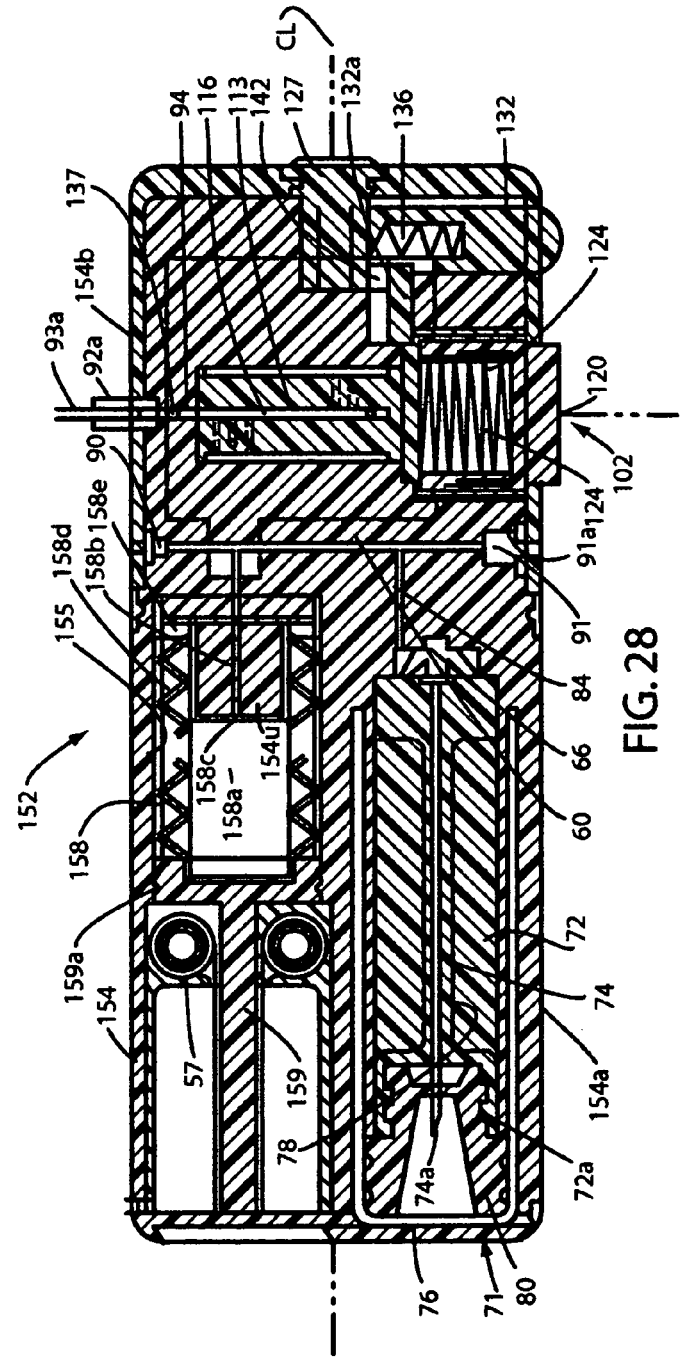
FIG. 28 is a cross-sectional view taken along lines 28-28 of FIG. 27.
Figure 29:
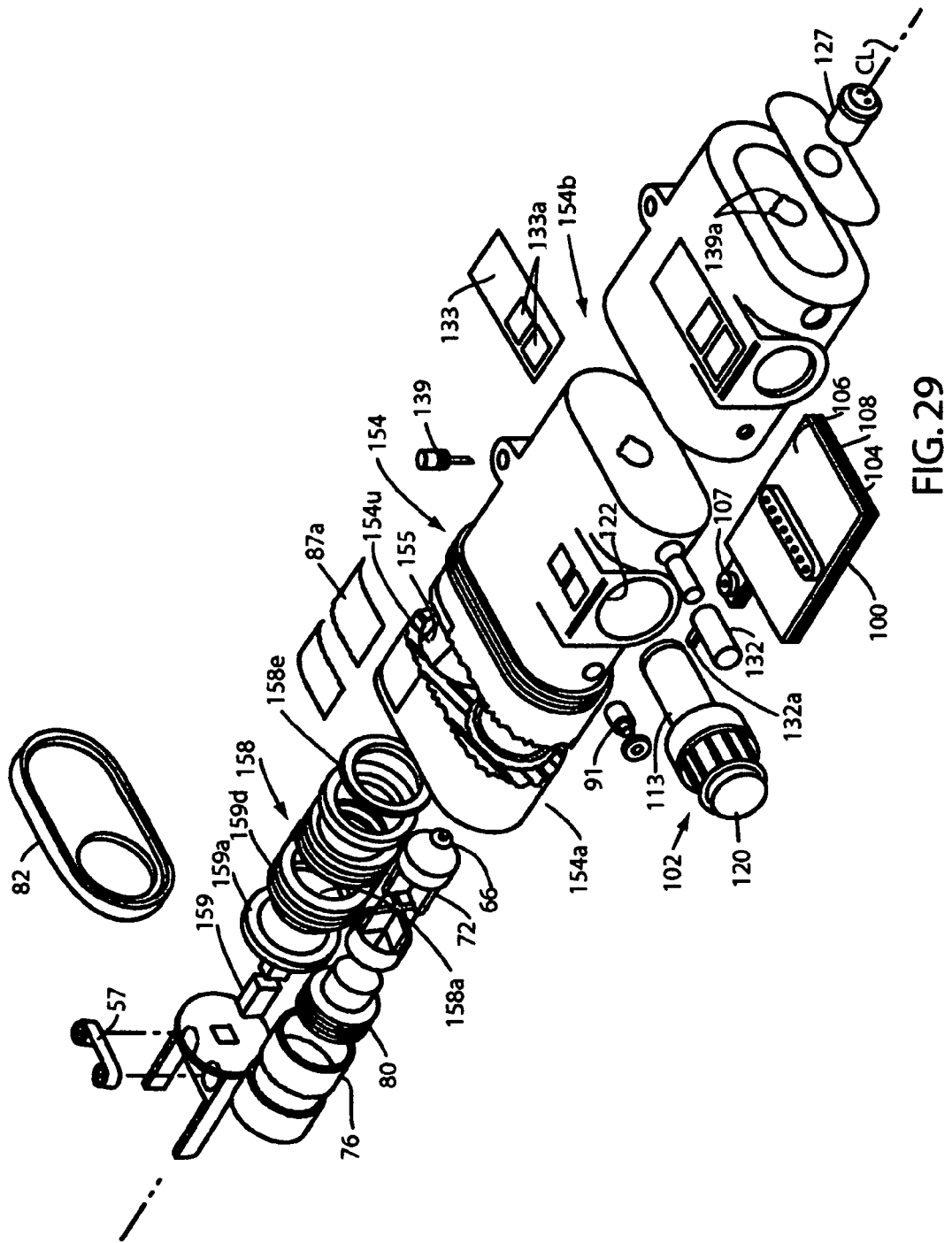
FIG. 29 is a generally perspective, exploded view of the fluid dispensing device of the form of the invention shown in FIG. 27.

Referring now to FIGS. 27 through 29, an alternate form of the fluid dispensing device of the present invention is there shown and generally designated by the numeral 152. This alternate embodiment is similar in many respects to the earlier described embodiment, and like numerals are used in FIGS. 27 through 29 to identify like components. As before, the apparatus here comprises a snap-together outer housing 154 having an axial centerline "CL" and first and second portions 154a and 154b respectively. Housing portion 154a houses the reservoir portion and the reservoir-fill portion, while housing portion 154b houses the flow control, the fluid delivery and the control portions of the apparatus. The reservoir-fill portion, the flow control portion, the fluid delivery portion and the control portion of this second form of the invention are substantially identical to those of the first embodiment. However, the reservoir portion 155, which is disposed within first portion 154a of outer housing 154, is somewhat different. The details of construction of this alternate form of reservoir portion will presently be described.

Also disposed within first portion 154a of outer housing 154 on one side of the axial centerline CL is the novel stored energy means of the invention for acting upon the fluid contained within the fluid reservoir in a manner to cause the fluid contained therewithin to controllably flow outwardly of the reservoir, through the flow control means of the invention and onwardly toward the patient. This important stored energy means here comprises a constant force spring member 57 that is carried within first portion 154a of the outer housing. Spring member 57, which is identical to that previously described, is first extended by fluid flowing into reservoir and then controllably retracts to cause fluid flow from the fluid reservoir through the flow control means of the invention, which is also identical to that previously described herein.

Considering once again the reservoir portion of this latest form of the apparatus, this portion here includes a novel expandable housing 158 defining a fluid reservoir 158a (FIGS. 28 and 29) that is provided with an inlet passageway 158b (FIG. 28) for permitting fluid flow into the fluid reservoir and an outlet 158c for permitting fluid flow from the fluid reservoir. Expandable housing 158, which can be constructed from a metal or plastic material and, as shown in FIG. 31B, can include a coating "C" of the character presently to be described, comprises a bellows structure having an expandable and compressible, accordion-like, annular-shaped sidewall 158d, the configuration of which is best seen in FIGS. 28 and 29. A capture ring 158e secures the expandable housing in position.

In this latest form of the invention, the stored energy means, or spring 57, acts upon inner expandable housing 158 in a manner to cause the fluid contained within fluid reservoir 158a to controllably flow outwardly of the housing, through the dispensing means of the invention and onwardly toward the patient. More particularly, after being expanded, spring 57 tends to uniformly return toward its starting configuration and, in so doing, will exert an inward pressure on a pusher means, shown here as pusher member 159 of the character shown in FIGS. 28 and 29. Pusher member 159 includes a pusher head 159a and is operably coupled with the expandable housing 158 (FIG. 28) and functions to move the expandable housing from an expanded configuration to a contracted configuration. More particularly, as the spring 57 returns toward its starting configuration, it will act on pusher member 159 in a manner to move the expandable housing from an expanded configuration to a contracted configuration shown in FIG. 31A and in so doing will cause the fluid contained within the fluid reservoir 158a to flow outwardly through outlet 158c and toward the flow rate control means and the administration set of the invention at a substantially constant rate. As the expandable housing contracts it will continue to move over housing ullage portion 154u ensuring that substantially all of the fluid contained in reservoir 158a will flow outwardly of outlet 158c.

An administration set which is identical to administration set 92 as previously described, is connected to the second portion 154b of housing 154 by a connector 92a in the manner shown in FIG. 28 of the drawings. The proximal end 93a of administration line 93 of the administration set is in communication with an outlet fluid passageway 94 which is formed in housing portion 154b in the manner best seen in FIG. 28.

As the fluid contained within reservoir 158a is urged outwardly thereof by the stored energy means, the fluid will flow under pressure through reservoir outlet 158c (FIG. 28) and then on toward the flow control means of this latest form of the invention. As before, the flow rate control means of the flow control means of this latest form of the invention comprises a rate control assembly 100 (FIG. 21) and a selector means, or selector assembly 102 (see also FIGS. 23 and 26) both of which are of the construction and operation previously described.

This latest form of the invention also includes disabling means for disabling the device and an alternate septum fill means for filling the fluid reservoir. The disabling means and septum fill means are identical to those previously described and include a septum 91 (FIG. 28) and a disabling shaft 135 that is telescopically movable within a passageway 137 formed within housing portion 154b (FIG. 5).

Turning next to FIGS. 30 through 32, still another form of the fluid dispensing device of the present invention is there shown and generally designated by the numeral 162. This latest embodiment is similar in many respects to the embodiment illustrated in FIGS. 27 through 29 and like numerals are used in FIGS. 30 through 32 to identify like components. As before, the apparatus here comprises a snap-together outer housing 164 having an axial centerline "CL" and first and second portions 164a and 164b respectively. Housing portion 164a houses the reservoir portion and the reservoir-fill portion, while housing portion 164b houses the flow control, the fluid delivery and the control portions of the apparatus. The reservoir portion, the flow control portion, the fluid delivery portion and the control portion of this third form of the invention are substantially identical to those of the second embodiment. However, the reservoir-fill portion 165 apparatus, which is disposed within first portion 164a of outer housing 164, is somewhat different. The details of construction of this alternate form of reservoir-fill portion will presently be described.

Also disposed within first portion 164a of outer housing 164 on one side of the axial centerline CL is the novel stored energy means of the invention for acting upon the fluid contained within fluid reservoir 158a in a manner to cause the fluid contained there within to controllably flow outwardly of the reservoir, through the flow control means of the invention and onwardly toward the patient. Fluid reservoir 158a is identical in construction and operation to the reservoir of FIGS. 27 through 29.

As before, the stored energy means here comprises a constant force spring member 57 that is carried within first portion 164a of the outer housing. Spring member 57, which is identical to that previously described, is first extended by fluid flowing into reservoir 158a and then controllably retracts to cause fluid flow from the fluid reservoir 158a, through the flow control means of the invention, which flow control means is also identical to that previously described herein.

Considering now the reservoir-fill portion 167 of the apparatus of this latest embodiment, this portion here includes a fill vial container 169 of a different construction. Fill vial 169 here comprises a cartridge fill vial having a hollow glass or plastic body portion 172 that defines a fluid chamber 172b. Fill vial 169 has an open first end 169a and a second end 174 that is closed by a pierceable, elastomeric septum 176. An elastomeric plunger 178 is reciprocally movable within fluid chamber 172b. As shown in FIG. 31, a hollow needle 180 is mounted within first portion 164a of the device housing and is located proximate the inboard end of chamber 182 which houses vial 169. Hollow needle 180 is adapted to pierce septum 176 when the fill vial 169 is inserted into chamber 182 and pushed into the position shown in FIG. 31. As the cover member 184, which closes chamber 182 and includes a pusher member 184a, is moved into a chamber closing position, pusher member 184a will urge elastomeric plunger 178 forwardly of fluid chamber 172b. As the plunger 178 moves inwardly of chamber 172b, the fluid contained within the chamber will be urged through hollow needle 180, past umbrella check valve 66, into passageway 84, into passageway 60 and then into the inlet 158c of the device for the reservoir, 158. As before, as the fluid enters the device reservoir, constant force spring 57 will be moved into the extended position shown in FIG. 31.

A number of beneficial agents can be contained within vial 169 and can be controllably dispensed to the patient including, by way of example, medicaments of various types, injectable drugs, injectable pharmaceuticals, hormones, antibodies, biologically active materials, elements, chemical compounds, or any other suitable material useful in diagnostic cure, medication, treatment or prevention of diseases or the maintenance of the good health of the patient.

An administration set which is identical to administration set 92 as previously described, is connected to the second portion 164b of housing 164 by a connector 92a in the manner shown in FIG. 31 of the drawings. The proximal end 93a of administration line 93 of the administration set is in communication with an outlet fluid passageway 94 which is formed in housing portion 164b in the manner best seen in FIG. 31.

As the fluid contained within reservoir 158a is urged outwardly thereof by the stored energy means, the fluid will flow under pressure through reservoir outlet 158c (FIG. 31) and then on toward the flow control means of this latest form of the invention. As before, the flow rate control means of the flow control means of this latest form of the invention comprises a rate control assembly 100 (FIG. 21) and a selector means, or selector assembly 102 (FIGS. 23 and 26) both of which are of the construction and operation previously described.

This latest form of the invention also includes septum fill means for filling the fluid reservoir and disabling means for disabling the device. The septum fill means and the disabling means are identical to those previously described and the septum fill and drug recovery means includes a pierceable septum 91 (FIG. 31) and the disabling means includes a disabling shaft 135 that is telescopically movable within a passageway 137 (FIG. 5) formed within housing portion 164b.

As was the case with the first embodiment of the invention, the second and third embodiments include priming means for purging and priming the various fluid delivery passageways of the device. This important priming means, which comprises prime channel 106k, functions to purge gases from the fluid delivery passageways and to prime the various fluidic elements of the device before the fluid is delivered to the fluid delivery line 93. This feature of the device ensures that only the desired fluid is delivered at the outlet port of the device during normal operation and that the device is in a state in which it will deliver fluid at the exit of the administration line in as short a time as possible.

The value of the priming means of the invention is evident from a study of FIG. 33 of the drawings which comprises a table of the fluidic properties of one form of the flow rate control member, or chip 106, of the flow rate selector means and the administration line for the device of the invention. For purposes of illustration in FIG. 33, the flow rates are shown to be 0.1 to 50 ml/hr and the rate defining channels are assumed to be from 400 $\mu m^2$ to 40,000 $\mu m^2$. Similarly, the priming channel is assumed to be 1000 $\mu m \times 100$ $\mu m$ wide×deep the channel in the rate control selector means is assumed to be 1 mm in diameter and 3 cm long and the administration line is assumed to be 1 meter long and 40 thousandths of an inch (approx. 1 mm) in diameter. The priming channels on the chip, the channel in the flow rate selector means and the administration line are treated as one item for the purpose of priming time and flow rate.

If the fluidic system is not compatible with the fluid being transported, either in terms of its biocompatibility or hyrdophilicity characteristics, a surface modification process will be needed. While not wanting to be held to a particular approach, the surface modification methodology may take one of several forms. One process that is extremely clean, fast and effective is plasma processing. In particular this technique allows for any of the following 1) plasma activation, 2) plasma induced grafting and 3) plasma polymerization of molecular entities on the surface of the bellows. For cases where an inert hydrophobic interface is desired, plasmas using hydrophilic molecules may be employed. That is, the channels' surface may be cleaned with an inert gas plasma, and subsequently, an appropriate plasma may be used to graft these molecule to the surface. Alternatively, if a hydrophobic surface is desired (e.g. for solutions that are highly corrosive or in oil-based solvents) an initial plasma cleaning may be done, followed by a plasma polymerization using hydrophobic monomers.

From a study of FIG. 33 it can be seen that if one of the flow rate defining fluidic micro-channels were used to prime the administration line, then there would be an unreasonably long time between the time that the device is initially "turned on" and the time that fluid is delivered from the administration line. Such a long time interval before the device is ready to use is undesirable in most applications of the device. It is evident that a priming means envisioned by this latest form of the device of the invention is an advantageous feature which enables the device to be ready to administer fluid in a matter of a minute or less.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing apparatus for dispensing fluids to a patient comprising:
   (a) a housing having a longitudinal centerline and a fluid reservoir for containing fluid to be dispensed to the patient, said fluid reservoir being provided with an inlet for permitting fluid flow into said fluid reservoir and an outlet for permitting fluid flow from said fluid reservoir, said housing further including an elongated vial receiving chamber;
   (b) pusher means disposed within said housing for movement between a first position and a second position to cause said fluid contained within said fluid reservoir to flow toward said outlet of said housing, said pusher means comprising a pusher member having a plunger end portion disposed within said fluid reservoir;
   (c) stored energy means disposed within said housing for acting upon said pusher means to cause said fluid pusher means to move toward said second position, said stored energy means comprising a constant force spring, said constant force spring comprising a high stress long deflection device that exerts a pressure directly on said pusher member causing said pusher member to act directly on the fluid within said fluid reservoir in a manner to cause the fluid to flow outwardly of said reservoir at a substantially constant rate;
   (d) fill means carried by said housing for filling said reservoir with the fluid to be dispensed, said fill means comprises a fill vial receivable within said vial receiving chamber;
   (e) flow control means carried by said housing for controlling fluid flow from said reservoir to the patient, said flow control means comprising:
      (i) a flow rate control assembly mounted within said housing, said flow rate control assembly including a flow rate control member having a surface and a plurality of micro channels formed therein, each of said micro channels having an outlet and an inlet and being of a selected length, depth and cross-sectional area; a distribution plate operably associated with said flow rate control member, said distribution plate having a plurality of flow control channels, each having an outlet and an inlet in communication with an outlet of a selected one of said micro channels; and a cover member operably associated with said distribution plate, said cover member having a fluid inlet port in communication with said fluid reservoir of said housing and a plurality of spaced apart fluid outlet ports in communication with said outlets of said plurality of flow control channels of said distribution plate; and
      (ii) a transversely extending selector member rotatably carried by said housing, said selector member having a head portion and a body portion, said body portion being superimposed over said flow rate control assembly and having a plurality of radially extending fluid passageways formed therein for selective communication with said plurality of spaced apart fluid outlet ports of said cover member upon rotation of said transversely extending selector member; and
   (f) dispensing means connected to said housing for dispensing fluids to the patient.

2. The apparatus as defined in claim 1 in which said housing further includes a cavity in communication with said inlet of said fluid reservoir and in which said fill means further comprises a pierceable septum disposed within said cavity.

3. The apparatus as defined in claim 1, further including volume indicator means carried by said housing for indicating the volume of fluid within said reservoir.

4. The apparatus as defined in claim 1, further including disabling means carried by said housing for preventing fluid flow toward the patient.

5. The apparatus as defined in claim 1 further including stop means for preventing rotation of said selector member.

6. The apparatus as defined in claim 1 in which said body portion of said selector member includes an axially-extending flow passageway.

7. The apparatus as defined in claim 1 in which said flow control means further comprises priming means for priming said fluidic flow control channels formed in said flow rate control assembly.

8. A dispensing apparatus for dispensing fluids to a patient comprising:
   (a) a housing having a longitudinal centerline and a fluid reservoir for containing fluid to be dispensed to the patient, said reservoir comprising a bellows structure having an expandable and compressible, accordion-like, annular-shaped sidewall expandable from a first contracted configuration to a second expanded configuration, said housing being provided with an inlet for permitting fluid flow into said fluid reservoir and an outlet for permitting fluid flow from said fluid reservoir;

(b) pusher means disposed within said housing for movement between a first position and a second position to cause said annular-shaped sidewall to move toward a contracted configuration and to cause said fluid contained within said fluid reservoir to flow toward said outlet of said housing, said pusher means comprising a pusher member having a pusher head, said pusher head being in direct engagement with said bellows structure to cause said expandable sidewall to move from said second expanded configuration to said first contracted configuration;

(c) stored energy means disposed within said housing for acting upon said pusher means to cause said fluid pusher means to move toward said second position, said stored energy means comprising a constant force spring, having spaced apart coiled portions located on either side of said pusher member and a strip portion connected to said coiled portions, said strip portion exerting a pressure directly on said pusher member causing said pusher member to act on the fluid within said fluid reservoir to cause the fluid to flow outwardly of said reservoir at a substantially constant rate;

(d) fill means carried by said housing for filling said reservoir with the fluid to be dispensed;

(e) flow control means carried by said housing for controlling fluid flow from said reservoir to the patient, said flow control means comprising:
  (i) a flow rate control assembly mounted within said housing, said flow rate control assembly including a flow rate control member having a plurality of fluidic flow control channels formed therein and a distribution plate operably associated with said flow rate control member;
  (ii) a transversely extending selector member rotatably carried by said housing, said selector member having a head portion and a body portion, said body portion being superimposed over, said flow rate control assembly and having a central passageway and plurality of radially extending fluid passageways formed therein in communication with said central passageway and with said distribution plate; and
  (iii) priming means for priming said plurality of fluidic flow control channels formed in said flow rate control member and said plurality of fluid passageways formed in said selector member with fluid from said reservoir; and (f) dispensing means connected to said housing for dispensing fluids to the patient.

9. The apparatus as defined in claim 8 in which said housing includes a cavity in communication with said inlet of said fluid reservoir and in which said fill means comprises a pierceable septum disposed within said cavity.

10. The apparatus as defined in claim 8 in which said housing includes a vial receiving chamber and in which said fill means comprises a fill vial receivable within said vial receiving chamber.

11. The apparatus as defined in claim 8, further including volume indicator means carried by said housing for indicating the volume of fluid within said reservoir.

12. The apparatus as defined in claim 8, further including disabling means carried by said housing for preventing fluid flow toward the patient.

13. The apparatus as defined in claim 8 further including stop means for preventing rotation of said selector member.

14. The apparatus as defined in claim 8 in which said body portion of said selector member includes an axially-extending flow passageway and a plurality of radially-extending flow passageways in communication with said axially-extending flow passageway.

15. The apparatus as defined in claim 8 in which said plurality of elongated fluidic flow control channels of said flow rate control member have a depth of approximately 10-100 μm.

16. The apparatus as defined in claim 8 in which said flow rate control assembly further includes a cover superimposed over said flow rate control member and a flow director member mounted intermediate said flow rate control member and said cover, said flow director member having a plurality of elongated fluidic flow control channels in communication with said plurality of fluid passageways formed in said flow rate control member.

17. The apparatus as defined in claim 16 in which said cover includes a plurality of fluid outlets and in which said plurality of elongated fluidic flow control channels in said flow director member are in communication with said plurality of fluid outlets of said cover.

18. A dispensing apparatus for dispensing fluids to a patient comprising:
  (a) a housing having a longitudinal centerline, a vial receiving chamber and a fluid reservoir for containing fluid to be dispensed to the patient, said reservoir comprising a bellows structure having an expandable and compressible, accordion-like, annular-shaped sidewall expandable from a first contracted configuration to a second expanded configuration, said housing being provided with an inlet for permitting fluid flow into said fluid reservoir and an outlet for permitting fluid flow from said fluid reservoir, said housing further including an ullage portion extending into said bellows structure for ensuring that substantially all of the fluid contained within the fluid reservoir will flow outwardly of said outlet;
  (b) pusher means disposed within said housing for movement between a first position and a second position to cause said annular-shaped sidewall to move toward a contracted configuration and to cause said fluid contained within said fluid reservoir to flow toward said outlet of said housing said pusher means comprising a pusher member having a pusher head in direct engagement with said bellows structure;
  (c) stored energy means disposed within said outer housing for acting upon said pusher means to cause said fluid pusher means to move toward said second position, said stored energy means comprising a constant force spring, said constant force spring comprising a high stress, long deflection device that exerts a pressure directly on said pusher member causing said pusher member to act on the fluid within said fluid reservoir to cause the fluid to flow outwardly of said reservoir at a substantially constant rate;
  (d) fill means carried by said housing for filling said reservoir with the fluid to be dispensed, said fill means comprising a fill vial receivable within said vial receiving chamber of said housing;
  (e) flow control means carried by said housing for controlling fluid flow from said reservoir to the patient, said flow control means comprising:
    (i) a flow rate control assembly mounted within said housing, said flow rate control assembly including a flow rate control plate having a surface and a plurality of longitudinally extending micro channels formed therein, said micro channels being of a selected length and depth and a top plate connected to said rate control plate, said flow rate control assembly further including a distribution plate operably associated with said flow rate control plate;

(ii) a transversely extending selector member rotatably carried by said housing, said selector member having a head portion and a body portion, said body portion being superimposed over, said flow rate control assembly and having a central passageway and a plurality of radially extending fluid passageways formed therein in communication with said central passageway and with said plurality of longitudinally extending micro channels; and (iii) priming means for priming said plurality of elongated micro-channels formed in said flow rate control member and said plurality of fluid passageways formed in said selector member with fluid from said reservoir;

(f) stop means for preventing rotation of said selector member; and (g) dispensing means connected to said housing for dispensing fluids to the patient.

19. The apparatus as defined in claim 18 in which said housing includes a cavity in communication with said inlet of said fluid reservoir and in which said fill means comprises a pierceable septum disposed within said cavity.

20. The apparatus as defined in claim 18, further including disabling means carried by said housing for preventing fluid flow toward the patient.

21. The apparatus as defined in claim 18 in which said body portion of said selector member includes an axially-extending flow passageway and a plurality of radially-extending flow passageways in communication with said axially-extending flow passageway.

22. The apparatus as defined in claim 18 in which said fluidic flow control channels have surfaces, said surfaces being modified to provide unique surface characteristics.

23. The apparatus as defined in claim 18 in which said flow control means further includes filter means for filtering fluids flowing from said reservoir toward said fluidic flow control channels of said flow rate control member.

* * * * *